(12) United States Patent
Li et al.

(10) Patent No.: US 11,932,617 B2
(45) Date of Patent: Mar. 19, 2024

(54) COMPOUND FOR USE IN RETINAL DISEASES

(71) Applicant: ZHUHAI UNITED LABORATORIES CO., LTD., Guangdong (CN)

(72) Inventors: Peng Li, Shanghai (CN); Xiaolin Li, Shanghai (CN); Zhi Luo, Shanghai (CN); Haiying He, Shanghai (CN); Guoping Hu, Shanghai (CN); Jian Li, Shanghai (CN); Shuhui Chen, Shanghai (CN)

(73) Assignee: ZHUHAI UNITED LABORATORIES CO., LTD., Guangdong (CN)

( * ) Notice: Subject to any disclaimer, the term of this patent is extended or adjusted under 35 U.S.C. 154(b) by 213 days.

(21) Appl. No.: 17/309,611

(22) PCT Filed: Dec. 18, 2019

(86) PCT No.: PCT/CN2019/126178
§ 371 (c)(1),
(2) Date: Jun. 10, 2021

(87) PCT Pub. No.: WO2020/125659
PCT Pub. Date: Jun. 25, 2020

(65) Prior Publication Data
US 2022/0127243 A1   Apr. 28, 2022

(30) Foreign Application Priority Data

Dec. 18, 2018 (CN) .......................... 201811550604.8
Dec. 4, 2019 (CN) .......................... 201911226373.X

(51) Int. Cl.
| | |
|---|---|
| C07D 401/04 | (2006.01) |
| A61P 27/02 | (2006.01) |
| C07D 213/73 | (2006.01) |
| C07D 401/06 | (2006.01) |
| C07D 401/12 | (2006.01) |

(52) U.S. Cl.
CPC ............ C07D 401/04 (2013.01); A61P 27/02 (2018.01); C07D 213/73 (2013.01); C07D 401/06 (2013.01); C07D 401/12 (2013.01)

(58) Field of Classification Search
CPC .. C07D 401/04; C07D 401/06; C07D 401/12; C07D 213/13; A61P 27/02
See application file for complete search history.

(56) References Cited

U.S. PATENT DOCUMENTS

| | | | |
|---|---|---|---|
| 10,913,722 B2 | 2/2021 | Jordan et al. | |
| 11,040,039 B2 | 6/2021 | Macdonald et al. | |
| 11,046,650 B2 | 6/2021 | Brady et al. | |
| 2018/0250306 A1 | 9/2018 | Brady | |
| 2018/0354905 A1 | 12/2018 | Brady | |
| 2021/0079179 A1 | 3/2021 | Alba et al. | |

FOREIGN PATENT DOCUMENTS

| | | | |
|---|---|---|---|
| CN | 101321742 A | | 12/2008 |
| CN | 108135867 | * | 6/2018 |
| CN | 108135867 A | | 6/2018 |
| CN | 108135907 A | | 6/2018 |
| JP | 2008542291 A | | 11/2008 |
| JP | 2018523700 A | | 8/2018 |
| JP | 2018530524 A | | 10/2018 |
| JP | 2020520127 A | | 7/2020 |
| JP | 2020536896 A | | 12/2020 |
| WO | 2018039197 A1 | | 3/2018 |
| WO | 2019075136 A1 | | 4/2019 |

OTHER PUBLICATIONS

Jan. 28, 2022 The 1st OA issued in AU2019409160 which is a counterpart application of the present invention.
Feb. 18, 2022 The 1st OA issued in CN2019800839597 which is a counterpart application of the present invention.
Jun. 28, 2022 Japanese Office Action issued in Japanese Patent Application No. 2021-535806.
Sep. 6, 2022 extended European Search Report issued in European Patent Application No. 19901226.1.
Sep. 20, 2022 Canadian First Office Action issued in Canadian Patent Application No. 3,123,473.
Choi W, Lian C, Ying L, Kim G E, You I C, Park S H, et al., Expression of lipid peroxidation markers in the tear film and ocular surface of patients with non-sjogren syndrome: potential biomarkers for dry eye disease, [J]. Curr Eye Res, 2016, 41(9):1143-1149.).
David Clark et al., Early Onset and Broad Activity of Reproxalap in a Randomized, Double-Masked, Vehicle-Controlled Phase 2b Trial in Dry Eye Disease, Am J Ophthalmol. Jun. 2021; 226:22-31.
Jul. 4, 2023 Korean Office Action issued in Korean Patent Application No. 10-2021-7022247.
Mar. 18, 2020 International Search Report issued in International Patent Application No. PCT/CN2019/126178.
Mar. 18, 2020 Written Opinion of the International Searching Authority issued in International Patent Application No. PCT/CN2019/126178.
Nov. 8, 2023 First Office Action issued in Mexican Patent Application No. MX/A/2021/007140.

* cited by examiner

*Primary Examiner* — D Margaret M Seaman
(74) *Attorney, Agent, or Firm* — Houston Beshining Law Office PLLC; Liangang Ye

(57) ABSTRACT

Provided is an aldehyde binder, specifically, disclosed is a compound as represented by formula (II) or a pharmaceutically acceptable salt.

6 Claims, 2 Drawing Sheets

COMPOUND FOR USE IN RETINAL DISEASES

The present application is a National Stage of International Application No. PCT/CN2019/126178, filed on Dec. 18, 2019, which claims priority of the Chinese Patent Application No. 201811550604.8 filed on Dec. 18, 2018 and the Chinese Patent Application No. 201911226373.X, filed on Dec. 4, 2019, the contents of which are incorporated herein by their entireties.

TECHNICAL FIELD

The present disclosure relates to an aldehyde binder, in particular to a compound represented by formula (II) or a pharmaceutically acceptable salt.

BACKGROUND

Xerophthalmia, also known as conjunctival xerosis, refers to a general term of a variety of diseases characterized by decreased tear film stability due to abnormal tear quality or quantity or kinetic abnormalities for any reasons, accompanied by eye discomfort (or) ocular surface tissue lesions, with specific discomfort symptoms manifested as eye irritation, visual disturbance, and tear film instability. Some of such syndromes are caused by ocular surface inflammation, resulting in loss of lacrimal functions. In addition, the syndromes are also associated with systemic autoimmunity.

Because some toxic aldehydes, such as malondialdehyde (MDA), 4-hydroxy-2-nonenal (4HNE), etc., are produced by metabolic mechanisms of in vivo or ocular tissues and organs, these aldehydes highly react with proteins, carbohydrates, grease, and DNA, resulting in chemically modified biomolecules to activate modulators of inflammatory molecules such as NF-kappaB, thereby causing injury to different organs, which is one of the triggers of xerophthalmia.

After studies by the present disclosure, a small-molecule drug enters the ocular inflammatory site in the form of eye drops or oral administration, through complexation reaction with aldehydes in vivo, thereby reducing aldehyde toxicity and decreasing inflammation to exerting the effect of treating xerophthalmia.

CONTENT OF THE INVENTION

The present disclosure provides a compound represented by formula (I) or a pharmaceutically acceptable salt thereof.

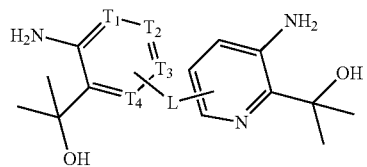

(I)

wherein $T_1$, $T_2$, $T_3$, and $T_4$ are each independently selected from N, C, and $CR_1$;

L is selected from a single bond, —O—, —S—, —$NR_2$— and —$(CR_3R_4)_n$—;

each $R_1$ is independently selected from H, F, Cl, Br, I, OH, and $NH_2$;

$R_2$ is selected from H and $C_{1-3}$ alkyl optionally substituted with 1, 2 or 3 $R_a$;

$R_3$ and $R_4$ are each independently selected from H, F, Cl, Br, I, OH, $NH_2$, CN and $C_{1-3}$ alkyl optionally substituted with 1, 2 or 3 $R_b$;

n is selected from 1, 2, and 3;

$R_a$ and $R_b$ are each independently selected from H, F, Cl, Br, I, OH, $NH_2$, CN, and $CH_3$ In some embodiments of the present disclosure, $R_2$ is selected from H, $CH_3$ and $CH_2CH_3$, wherein the $CH_3$ and the $CH_2CH_3$ are optionally substituted with 1, 2 or 3 $R_a$, and other variables are as defined in the present disclosure.

In some embodiments of the present disclosure, $R_2$ is selected from H, $CH_3$ and $CH_2CH_3$, and other variables are as defined in the present disclosure.

In some embodiments of the present disclosure, $R_3$ and $R_4$ are each independently selected from H, F, Cl, Br, I, OH, $NH_2$, CN, $CH_3$ and $CH_2CH_3$, wherein the $CH_3$ and the $CH_2CH_3$ are optionally substituted with 1, 2, or 3 $R_b$, and other variables are as defined in the present disclosure.

In some embodiments of the present disclosure, $R_3$ and $R_4$ are each independently selected from H, F, Cl, Br, I, OH, $NH_2$, CN, $CH_3$ and $CH_2CH_3$, and other variables are as defined in the present disclosure.

In some embodiments of the present disclosure, L is selected from a single bond, —O—, —S—, —NH—, —$(CH_2)_2$— and —$CH_2$—, and other variables are as defined in the present disclosure.

The present invention provides a compound represented by formula (II) or a pharmaceutically acceptable salt thereof,

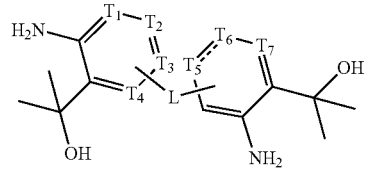

(II)

wherein

⟋⟋ is selected from a single bond and a double bond;

$T_1$, $T_2$, $T_3$, and $T_4$ are each independently selected from N, C, and $CR_1$;

$T_5$ is selected from C, $CR_5$, and C=O;

$T_6$ is selected from C, $CR_6$, and N;

$T_7$ is selected from N and $CR_7$;

when $T_5$ is selected from C=O and $T_6$ is selected from N, then ⟋⟋ is selected from a single bond;

L is selected from a single bond, —O—, —S—, —$NR_2$— and —$(CR_3R_4)_n$—;

each $R_1$ is independently selected from H, F, Cl, Br, I, OH, and $NH_2$;

$R_2$ is selected from H and $C_{1-3}$ alkyl optionally substituted with 1, 2 or 3 $R_a$;

$R_3$ and $R_4$ are each independently selected from H, F, Cl, Br, I, OH, $NH_2$, CN and $C_{1-3}$ alkyl optionally substituted with 1, 2 or 3 $R_b$;

$R_5$, $R_6$ and $R_7$ are each independently selected from H, F, Cl, Br and I;

n is selected from 1, 2, and 3;

$R_a$ and $R_b$ are each independently selected from H, F, Cl, Br, I, OH, $NH_2$, CN, and $CH_3$.

In some embodiments of the present disclosure, $R_2$ is selected from H, $CH_3$ and $CH_2CH_3$, wherein the $CH_3$ and the CH₂CH₃ are optionally substituted with 1, 2 or 3 R$_a$, and other variables are as defined in the present disclosure.

In some embodiments of the present disclosure, R$_2$ is selected from H, CH$_3$ and CH$_2$CH$_3$, and other variables are as defined in the present disclosure.

In some embodiments of the present disclosure, R$_3$ and R$_4$ are each independently selected from H, F, Cl, Br, I, OH, NH$_2$, CN, CH$_3$ and CH$_2$CH$_3$, wherein the CH$_3$ and the CH$_2$CH$_3$ are optionally substituted with 1, 2, or 3 R$_b$, and other variables are as defined in the present disclosure.

In some embodiments of the present disclosure, R$_3$ and R$_4$ are each independently selected from H, F, Cl, Br, I, OH, NH$_2$, CN, CH$_3$ and CH$_2$CH$_3$, and other variables are as defined in the present disclosure.

In some embodiments of the present disclosure, L is selected from a single bond, —O—, —S—, —NH—, —(CH$_2$)$_2$— and —CH$_2$—, and other variables are as defined in the present disclosure.

Some embodiments of the present disclosure are derived from any combination of the variables described above.

In some embodiments of the present disclosure, the compound described above or a pharmaceutically acceptable salt thereof is selected from

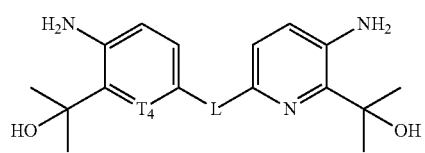
(I-1)

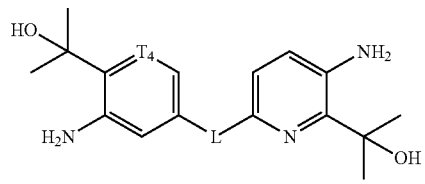
(I-2)

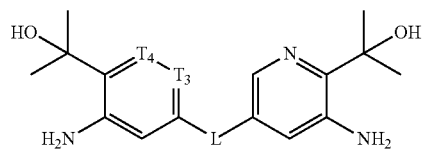
(I-3)

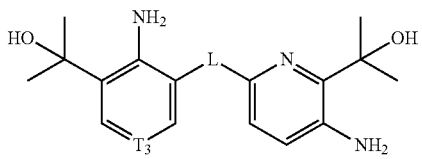
(II-1)

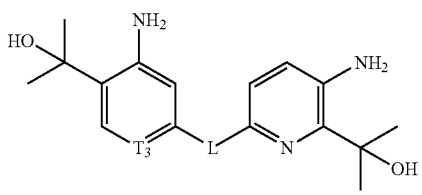
(II-2)

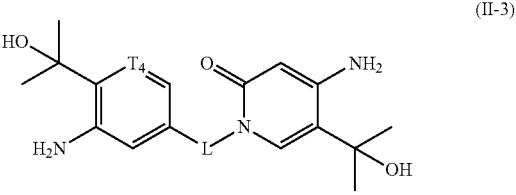
(II-3)

wherein

T$_3$ and T$_4$ are each independently selected from N and CR$_1$;

R$_1$ and L are as defined in the present disclosure.

In some embodiments of the present disclosure, the compound described above or a pharmaceutically acceptable salt thereof is selected from

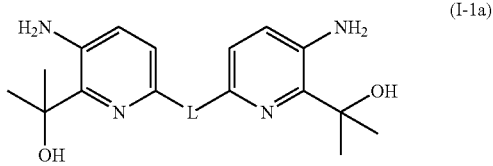
(I-1a)

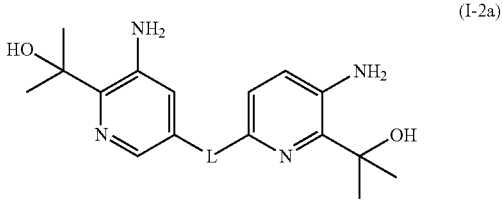
(I-2a)

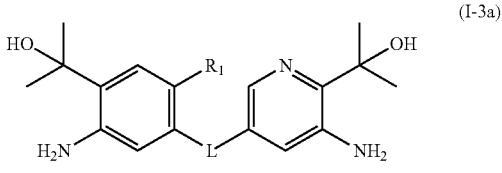
(I-3a)

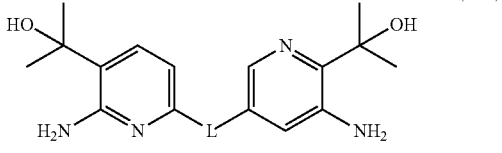
(I-3b)

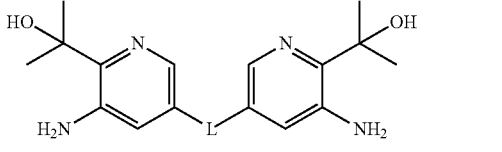
(I-3c)

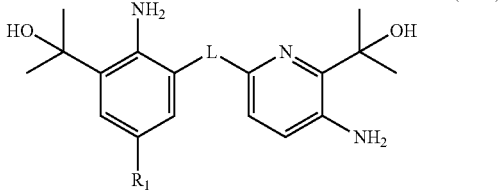
(II-1a)

-continued

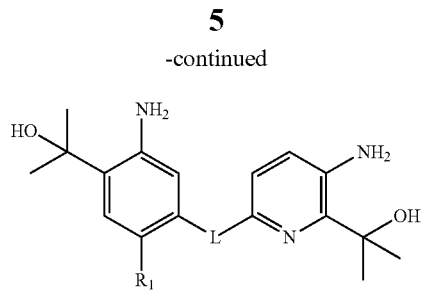
(II-2a)

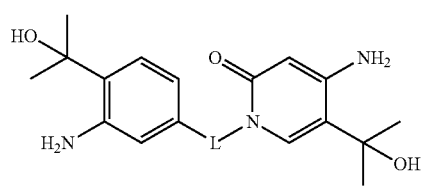
(II-3a)

wherein

R₁ and L are as defined in the present disclosure.

The present disclosure also provides a compound represented by the following formula or a pharmaceutically acceptable salt thereof, wherein the compound represented by the following formula or the pharmaceutically acceptable salt thereof is selected from:

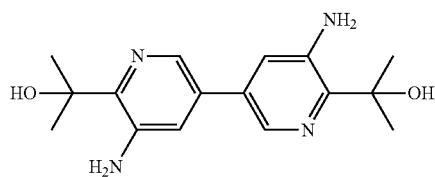

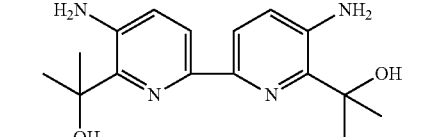

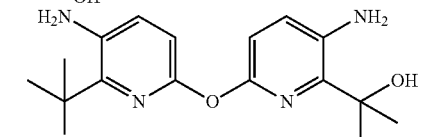

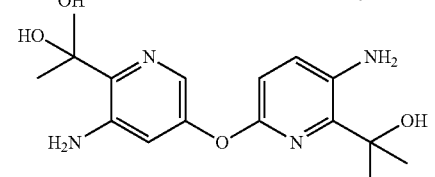

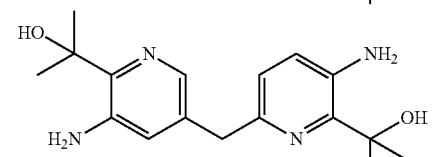

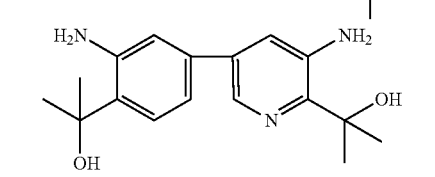

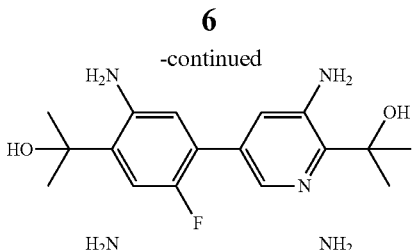

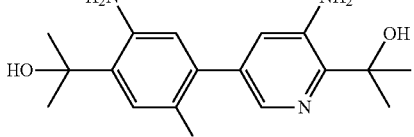

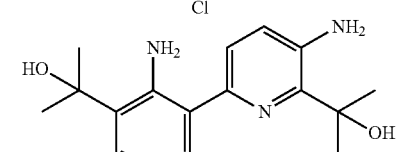

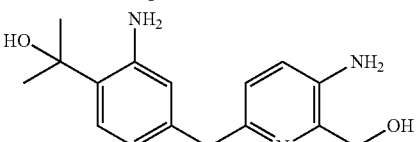

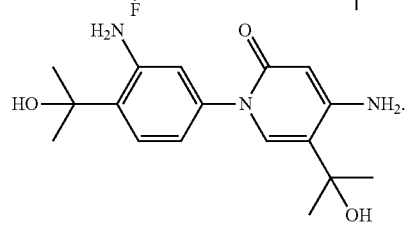

The present disclosure also provides a pharmaceutical composition comprising a therapeutically effective amount of the compound, or the pharmaceutically acceptable salt thereof as an active ingredient, and a pharmaceutically acceptable carrier.

In some embodiments of the present disclosure, the compound or pharmaceutically acceptable salts thereof or the use of the composition in the manufacture of the medicament related to aldehyde binder.

In some embodiments of the present disclosure, in the use described above, the medicament related to aldehyde binder is used for the treatment of xerophthalmia.

Definition and Explanation

Unless otherwise stated, the following terms and phrases used herein are intended to have the following meanings. A particular term or phrase should not be considered uncertain or unclear if not specially defined, but should be understood in its ordinary meaning. When a trade name appears herein, it is intended to refer to its corresponding commodity or its active ingredient. The term "pharmaceutically acceptable" used herein refers to those compounds, materials, compositions and/or dosage forms that are within the scope of reliable medical judgment, suitable for use in contact with human and animal tissues, without excessive toxicity, irritation, allergic reactions or other problems or complications, and commensurate with a reasonable benefit/risk ratio.

The term "pharmaceutically acceptable salt" refers to a salt of a compound of the present disclosure that is prepared from a compound with a specific substituent found in the present disclosure with a relatively nontoxic acid or base. When the compound of the present disclosure contains a relatively acidic functional group, a base addition salt can be obtained by a neutral contact between a sufficient amount of base and such compounds in a pure solution or a suitable inert solvent. The pharmaceutically acceptable base addition salt includes sodium, potassium, calcium, amine, organic amine or magnesium salts, or similar salts. When the compound of the present disclosure contains a relatively basic functional group, an acidic addition salt can be obtained by a neutral contact between a sufficient amount of acid and such compounds in a pure solution or a suitable inert solvent. Examples of the pharmaceutically acceptable acid addition salt include salts of inorganic acids including, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, etc., salts of organic acids including, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid, and similar acids, salts of amino acids such as arginine, etc., and salts of organic acids such as glucuronic acid, etc. Some specific compounds of the present disclosure contain basic and acidic functional groups so that the compounds can be converted to either base or acid addition salts.

The pharmaceutically acceptable salt of the present disclosure can be synthesized by parent compounds containing acid radicals or bases with conventional chemical methods. In general, such salts are prepared by reacting the compounds in forms of free acids or bases with stoichiometrically appropriate bases or acids in water or an organic solvent or a mixture thereof.

In addition to the salt form, the compound provided by the present disclosure also has a prodrug form. The prodrug of the compound described herein readily has chemical changes under physiological conditions so that the prodrug is converted into the compound of the present disclosure. In addition, the prodrug may be converted into the compound of the present disclosure in the in vivo environment by chemical or biochemical methods.

Some compounds of the present disclosure may be present in an unsolvated or solvated form, including a hydrate form. Generally, the solvated form is comparable to the unsolvated form, both of which are within the scope of the present disclosure.

Optically active (R)- and (S)-isomers and D and L isomers can be prepared by chiral synthesis or chiral reagents or other conventional techniques. If one enantiomer of some compound of the present disclosure is desired, the enantiomer can be prepared by asymmetric synthesis or derivatization with a chiral auxiliary, wherein the obtained diastereo-isomer mixture is separated and an auxiliary group splits to provide a pure desired enantiomer. Alternatively, when a molecule contains a basic functional group (such as amino) or an acidic functional group (such as carboxyl), a salt of the diastereo-isomer is formed by the functional group with a suitably optically active acid or base, and the diastereoisomer is resolved by a conventional method known in the art and then recovered to obtain a pure enantiomer. In addition, the separation of the enantiomer and the diastereoisomer is usually completed by using chromatography, wherein the chromatography employs a chiral stationary phase and is optionally combined with chemical derivatization (e.g., formation of carbamate from amine). The compound of the present disclosure may contain atomic isotopes in unnatural proportions on one or more atoms constituting the compound. For example, the compound may be labeled by radioactive isotopes, such as tritium ($^3$H), iodine-125 ($^{125}$I) or C-14 ($^{14}$C). For example, hydrogen can be substituted with heavy hydrogen to form a deuterated drug, and a bond composed of the tritium and carbon is stronger than that of ordinary hydrogen and carbon. Compared with a non-deuterated drug, the deuterated drug has the advantages of reduced toxic and side effects, increased drug stability, enhanced efficacy, prolonged biological half-life of the drug, etc. All transformations in all isotopic compositions of the compound of the present disclosure, whether radioactive or not, are included within the scope of the present disclosure.

The term "optional" or "optionally" refers to that an event or condition described herein below may or may not occur, and the description includes presence of the event or condition and absence of the event or condition.

The term "substituted" refers to that any one or more hydrogen atoms on a particular atom are substituted with a substituent, wherein the substituent may include variants of heavy hydrogen and hydrogen, provided that a valence state of the particular atom is normal and the substituted compound is stable. When the substituent is oxygen (i.e. =O), two hydrogen atoms are substituted. Oxygen substitution does not occur on aryl. The term "optionally substituted" means that the atom may be substituted or unsubstituted; unless otherwise specified, the type and number of substituents can be arbitrary provided that the substituents can be chemically realized.

When any variable (e.g. R) appears more than once in the composition or structure of the compound, the definition of the variable in each case is independent. Therefore, for example, if one group is substituted with 0-2 Rs, the group may optionally be substituted with at most 2 Rs, and the R has an independent option in each case. Furthermore, combinations of the substituents and/or variants thereof are allowed only if such combinations result in stable compounds.

When the number of linking groups is 0, e.g. —(CRR)0- indicates that the linking group is a single bond.

When one of the variables is selected from the single bond, two groups linked by the single bond are directly linked, for example, when L in A-L-Z represents the single bond, the structure is actually A-Z.

When one substituent is vacant, the substituent is absent, for example, when X in A-X is vacant, the structure is actually A. When the listed substituents do not indicate by which atom the substituents are linked to the substituted group, such substituents can be bonded through any atom thereof, for example, pyridyl as the substituent can be linked to the substituted group through any carbon atom on a pyridine ring. When the listed linking group does not indicate a linking direction thereof, the linking direction thereof is arbitrary, e.g., the linking group L in

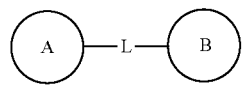

is -M-W-, at which time the -M-W- not only can be linked to rings A and B in the same direction as the reading order from left to right to constitute

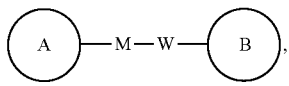

but also can be linked to the rings A and B in the opposite direction as the reading order from left to right to constitute

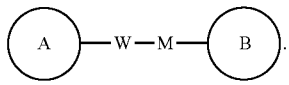

Combinations of the linking group, the substituents and/or variants thereof are allowed only if such combinations result in stable compounds.

Unless otherwise specified, the term "$C_{1-6}$ alkyl" is used to represent a linear or branched saturated hydrocarbon group consisting of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl, etc.; $C_{1-6}$ alkyl may be monovalent (e.g. methyl), divalent (e.g., methylene), or multivalent (e.g., methyne). Examples of $C_{1-6}$ alkyl include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl), hexyl, etc.

Unless otherwise specified, the term "$C_{1-3}$ alkyl" is used to represent a linear or branched saturated hydrocarbon group consisting of 1 to 6 carbon atoms. The $C_{1-3}$ alkyl includes $C_{1-2}$ and $C_{2-3}$ alkyl, etc.; the $C_{1-3}$ alkyl may be monovalent (e.g. methyl), divalent (e.g., methylene), or multivalent (e.g., methyne). Examples of $C_{1-3}$ alkyl include, but are not limited to, methyl (Me), ethyl (Et), propyl (including n-propyl and isopropyl), etc.

Unless otherwise specified, the term "$C_{1-3}$ alkoxy" represents those alkyl groups which are linked to the reset of a molecule by one oxygen atom and contains 1 to 3 carbon atoms. The $C_{1-3}$ alkoxy includes $C_{1-2}$, $C_{2-3}$, $C_3$ and $C_2$ alkoxy, etc. Examples of $C_{1-3}$ alkoxy include, but are not limited to, methoxy, ethoxy, propoxy (including n-propoxy and isopropoxy), etc.

Unless otherwise specified, $C_{n-n+m}$ or $C_n-C_{n+m}$ includes any particular case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and furthermore includes any one range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{-12}$, etc.; similarly, n membered to n+m membered indicates that the number of atoms on the ring is from n to n+m, for example, a 3-12 membered ring includes a 3 membered ring, a 4 membered ring, a 5 membered ring, a 6 membered ring, a 7 membered ring, an 8 membered ring, a 9 membered ring, a 10 membered ring, an 11 membered ring, and a 12 membered ring, and furthermore includes any one range from n to n+m, for example, a 3-12 membered ring includes a 3-6 membered ring, a 3-9 membered ring, a 5-6 membered ring, a 5-7 membered ring, a 6-7 membered ring, a 6-8 membered ring, a 6-10 membered ring, etc.

The term "leaving group" refers to a functional group or an atom that may be substituted with another functional group or atom by a substitution reaction (e.g., an affinity substitution reaction). For example, representative leaving groups include trifluoromethanesulfonate, chlorine, bromine, iodine, sulfonate such as methanesulfonate, toluenesulfonate, p-bromobenzenesulfonate, p-toluenesulfonate, etc., acyloxy such as acetoxyl, trifluoroacetoxy, etc.

The term "protective group" includes, but is not limited to, "an amino protective group", "a hydroxy protective group", or "a sulfydryl protective group". The term "amino protective group" refers to a protective group suitable for preventing side reactions at a nitrogen position of the amino. Representative amino protective groups include, but are not limited to, formyl, acyl, such as alkanoyl (e.g., acetyl, trichloroacetyl, or trifluoroacetyl), alkoxycarbonyl, such as tert-butoxycarbonyl (Boc), arylmethoxycarbonyl, such as benzyloxycarbonyl (Cbz) and 9-fluorenylmethoxycarbonyl (Fmoc), arylmethyl, such as benzyl (Bn), triphenylmethyl (Tr), 1,1-di-(4'-methoxyphenyl) methyl, silyl such as trimethylsilyl (TMS), tert-butyldimethylsilyl (TBS), etc. The term "hydroxyl protective group" refers to a protective group suitable for preventing side reactions of hydroxyl. Representative hydroxyl protective groups include, but are not limited to, alkyl, such as methyl, ethyl, and tert-butyl, acyl, such as alkanoyl (e.g., acetyl), arylmethyl, such as benzyl (Bn), p-methoxybenzyl (PMB), 9-fluorenylmethyl (Fm), and diphenylmethyl (DPM), silyl, such as trimethylsilyl (TMS), tert-butyldimethylsilyl (TBS), etc.

The compound of the present disclosure can be prepared by a variety of synthetic methods known to those skilled in the art, including specific embodiments listed below, embodiments formed in combination with other chemical synthesis methods, and equivalent substitutions known to those skilled in the art. Preferred embodiments include, but are not limited to, examples of the present disclosure.

The solvent used in the present disclosure is commercially available. The following abbreviations are used in the present disclosure: aq represents water; HATU represents O-(7-azabenzotriazol-1-yl)-N,N,N',N'-tetramethylurea hexafluorophosphate; EDC represents N-(3-dimethylaminopropyl)-N'-ethylcarbodiimide hydrochloride; m-CPBA represents 3-chloroperoxybenzoic acid; eq represents equivalent and equal amount; CDI represents carbonyl diimidazole; DCM represents dichloromethane; PE represents PE; DIAD represents diisopropyl azodicarboxylate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amine protective group; BOC represents tert-butoxycarbonyl, which is an amine protective group; HOAc represents acetic acid; $NaCNBH_3$ represents sodium cyanoborohydride; r.t. represents room temperature; O/N represents overnight; THF represents tetrahydrofuran; $Boc_2O$ represents di-tert-butyl dicarbonate; TFA represents trifluoroacetic acid; DIPEA represents diisopropylethylamine; $SOCl_2$ represents thionyl chloride; $CS_2$ represents carbon disulfide; TsOH represents p-toluenesulfonic acid; NFSI represents N-fluoro-N-(benzenesulfonyl) benzenesulfonate amide; NCS represents N-chlorosuccinimide; n-$Bu_4$NF represents tetrabutylammonium fluoride; iPrOH represents 2-propanol; mp represents melting point; LDA represents lithium diisopropylamide; LiHMDS represents lithium hexamethyldisilazide; Xantphos represents 4,5-bisdiphenylphosphine-9,9-dimethylxanthene; $LiAlH_4$ represents lithium aluminum hydride; $Pd(dba)_2$ represents tris(dibenzylideneacetone) dipalladium; mCPBA represents m-chloroperoxybenzoic acid; pd(dppf)$Cl_2$ represents [1,1'-bis(diphenylphosphino) ferrocene] dichloropalladium (II); DBU represents 1,8-diazabicyclo[5.4.0] undec-7-ene.

Compounds are named according to conventional nomenclature principles in the art or using ChemDraw® software, and commercially available compounds are named in the vendor's catalogue.

TECHNICAL EFFECT

Figure 1:
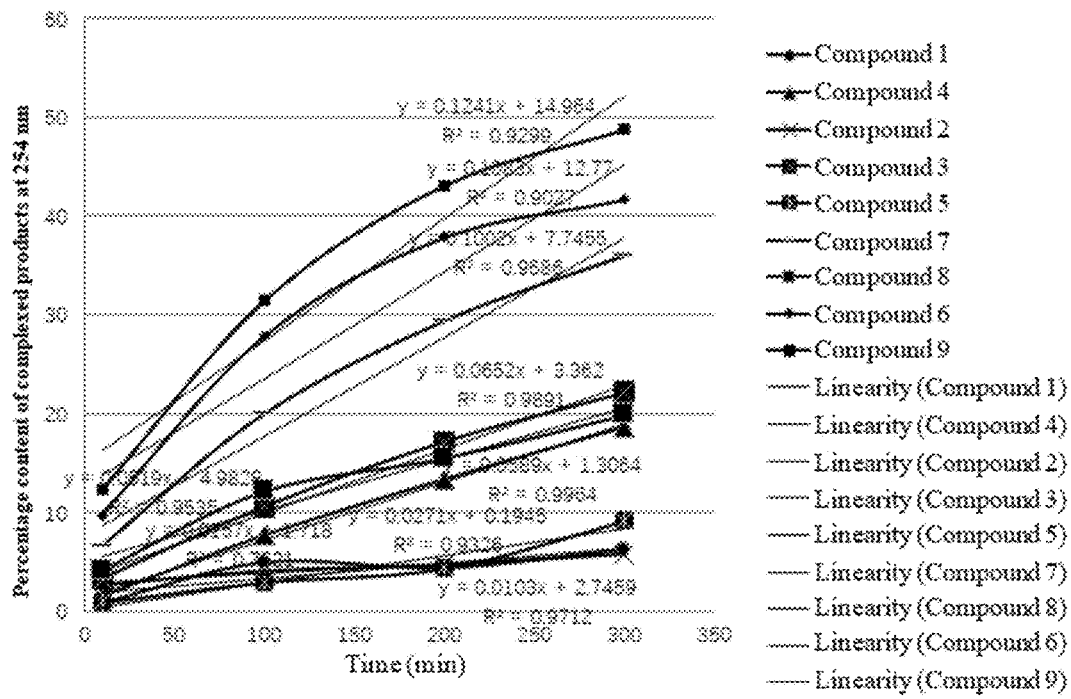
FIG. 1: Test results of in vitro aldehyde capture capacity.

The compound of the present disclosure has excellent aldehyde complexing capacity, and is helpful to remit eye inflamed, thereby treating the xerophthalmia.

DETAILED DESCRIPTION OF THE EMBODIMENT

The following examples further illustrate the present disclosure, but the present disclosure is not adversely limited thereto. The present disclosure has been described in detail herein, wherein specific embodiments thereof are also disclosed, and it will be apparent to those skilled in the art to make various changes and improvements to specific embodiments of the present disclosure without departing from the spirit and scope of the present disclosure.

Example 1: Synthesis of Compound 1

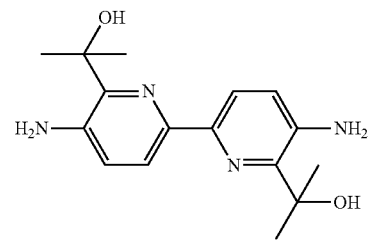

Synthetic Route of the Compound 1

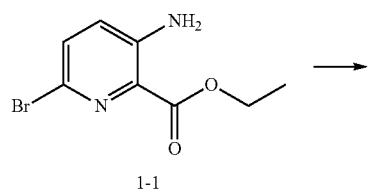

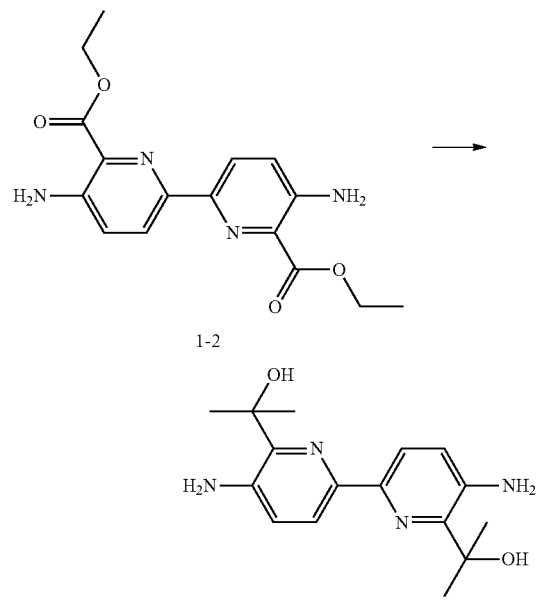

Step 1: Synthesis of Compound 1-2

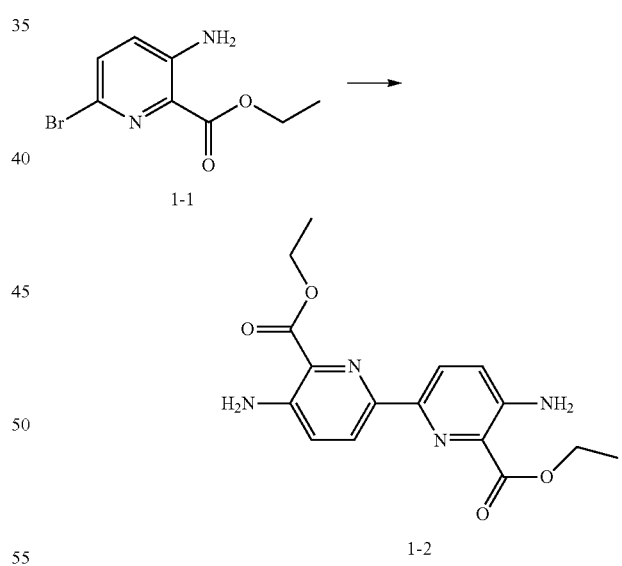

A Compound 1-1 (1.5 g, 6.12 mmol, 1 eq), hexamethylditin (1.60 g, 4.90 mmol, 1.02 mL, 0.8 eq) and bis (tri-tert-butylphosphine) palladium(0) (938.39 mg, 1.84 mmol, 0.3 eq) were dissolved in toluene (20 mL), and stirred at 80° C. for 14 hours. TLC spot plate (dichloromethane:methanol=10:1) was used to test if the reaction was complete, and samples were concentrated and stirred directly. The samples were purified by a rapid silica gel column (mobile phase: 0-10% dichloromethane/methanol) to obtain Compound 1-2. $[M+1]^+=330.9$

Step 2: Synthesis of Compound 1

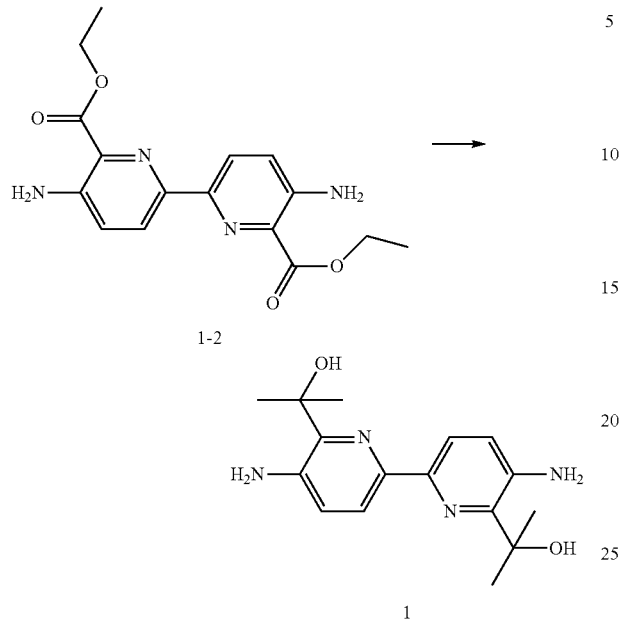

A substrate 1-2 (200 mg, 605 μmol, 1 eq) was dissolved in tetrahydrofuran (20 mL), methyl magnesium bromide (3 M, 4.04 mL, 20 eq) was slowly added dropwise at 0° C., and the mixture was reacted under stirring at 0° C. for 2 hours. A reaction solution was quenched by adding water (20 mL), then extracted with ethyl acetate (50 mL*3), and concentrated for organic phases. The mixture was dissolved in dimethylformamide (DMF) and purified by HPLC (neutral) to obtain Compound 1.

$^1$H NMR (400 MHz, DMSO-d$_6$) δ 7.80 (d, J=8.3 Hz, 2H), 7.00 (d, J=8.3 Hz, 2H), 5.56 (s, 4H), 5.47 (s, 2H), 1.56 (s, 12H); LCMS: [M+H]$^+$=302.9

Example 2: Synthesis of Compound 2

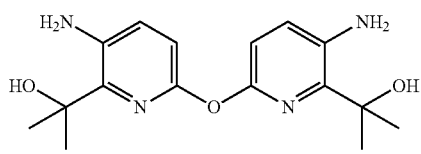

Synthetic Route of Compound 2

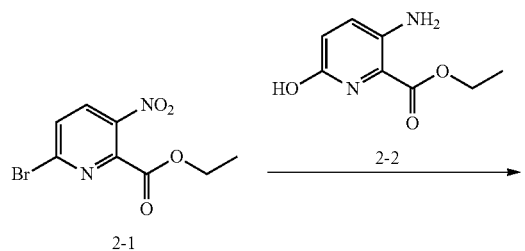

Step 1: Synthesis of Compound 2-3

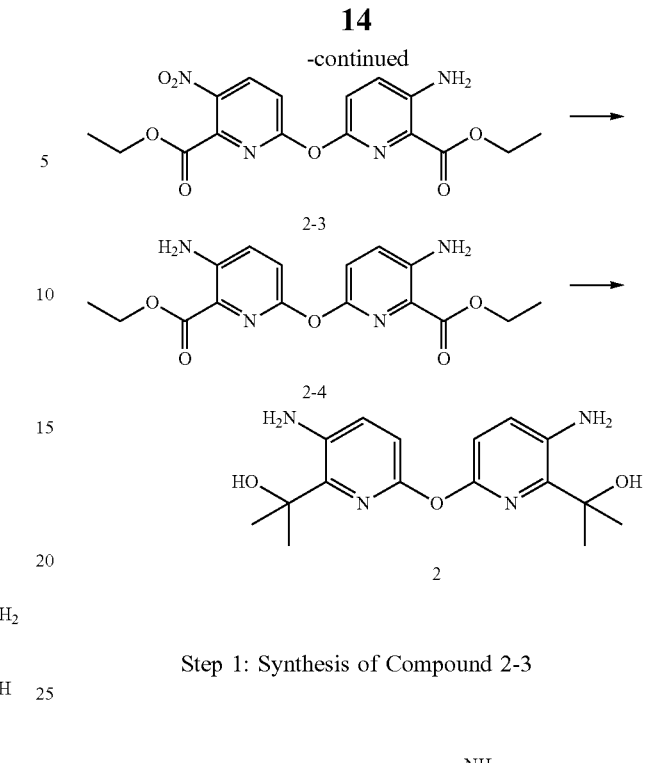

Substrates 2-1 (702.07 mg, 2.55 mmol, 1.5 eq) and 2-2 (310 mg, 1.70 mmol, 1 eq) were dissolved in acetonitrile (20 mL), cesium carbonate (1.11 g, 3.40 mmol, 2 eq) was added, and the mixture was reacted under stirring at 50° C. for 3 hours. After the reaction was over, a reaction solution was filtered directly, and filtrate was spin-dried to obtain crude. The crude was purified by a rapid silica gel column (petroleum ether:ethyl acetate=100:0 to 60:40) to obtain Compound 2-3.

$^1$H NMR (400 MHz, CDCl$_3$) δ 8.42 (d, J=9.03 Hz, 1H), 7.24 (d, J=4.02 Hz, 1H), 7.15-7.20 (m, 1H), 7.07-7.13 (m, 1H), 5.82 (br s, 2H), 4.39 (dq, J=4.27, 7.11 Hz, 4H), 1.35 (td, J=7.15, 18.57 Hz, 6H).

Step 2: Synthesis of Compound 2-4

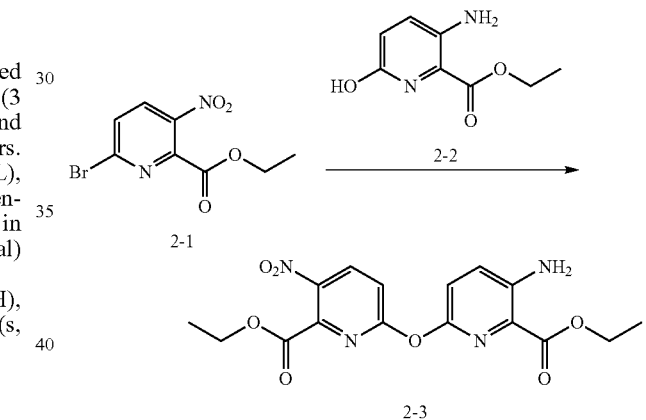

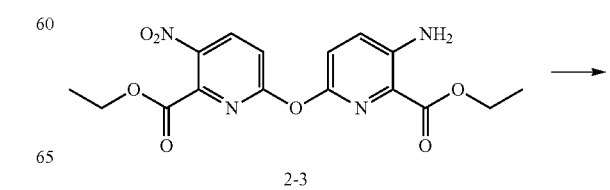

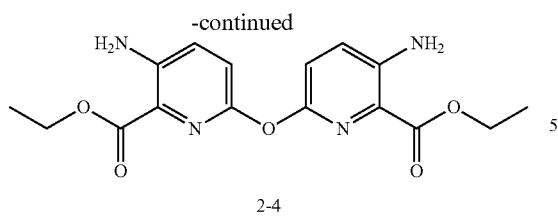

2-4

The Compound 2-3 (360 mg, 956.63 μmol, 1 eq) and hydrochloric acid (12 M, 478.32 μL, 6 eq) were dissolved in ethanol (20 mL) and water (5 mL); reducing iron powders (534.23 mg, 9.57 mmol, 10 eq) were added, and stirred at 25° C. for 2 hours. After the reaction was over, a reaction solution was adjusted to pH=9 with a saturated sodium carbonate aqueous solution (30 mL), and extracted with ethyl acetate (30 mL*2). After organic phases were combined, the organic phases were dried over anhydrous sodium sulfate and spin-dried to obtain crude. The crude was purified by a rapid silica gel column (petroleum ether:ethyl acetate=100:0 to 40:60) to obtain Compound 2-4.

$^{1}$H NMR (400 MHz, CDCl$_3$) δ 7.17-7.24 (m, 2H), 7.09-7.16 (m, 2H), 5.64 (br s, 4H), 4.37 (q, J=7.03 Hz, 4H), 1.37 (t, J=7.03 Hz, 6H).

Step 3: Synthesis of Compound 2

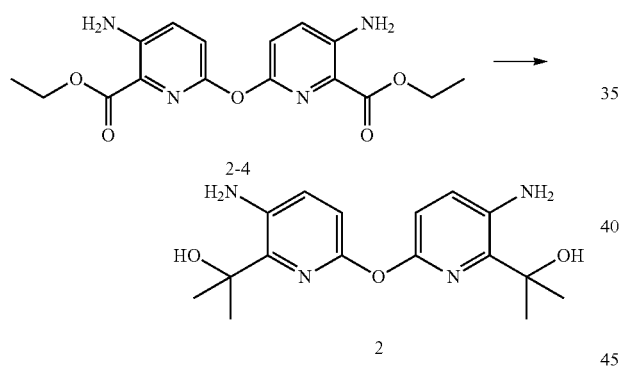

The Compound 2-4 (120 mg, 346.48 μmol, 1 eq) was dissolved in tetrahydrofuran (10 mL) and cooled to 0° C. Methyl magnesium bromide (3 M, 3.00 mL, 26 eq) was added dropwise in a 2-methyltetrahydrofuran solution at 0° C. The solution was reacted under stirring at 0° C. for 30 min, and then stirred at 25° C. for 2 hours. After the reaction was over, a reaction solution was quenched by adding a saturated amine chloride aqueous solution (40 mL), and then extracted with ethyl acetate (100 mL). The organic phases were dried over anhydrous sodium sulfate and spin-dried to obtain the crude. The crude was purified by HPLC separation (column model: Waters Xbridge 150*25 mm 5 μm; mobile phase: [water (10 mM amine bicarbonate solution)-acetonitrile]; % B (acetonitrile): 0%-50%, 10 min) to obtain Compound 2.

LCMS: [MS+H$^+$]=318.9.

$^{1}$H NMR (400 MHz, DMSO-d$_6$) δ 7.03 (d, J=8.28 Hz, 2H), 6.57 (d, J=8.53 Hz, 2H), 5.37 (s, 2H), 5.27 (s, 4H), 1.38 (s, 12H).

Example 3: Synthesis of Compound 3

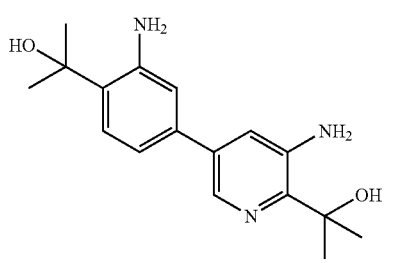

3

Synthetic Route of Compound 3

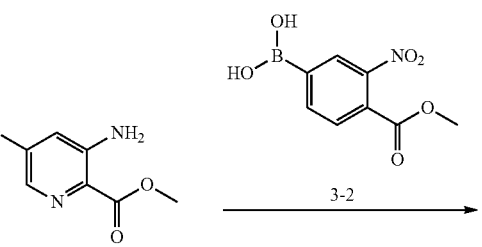

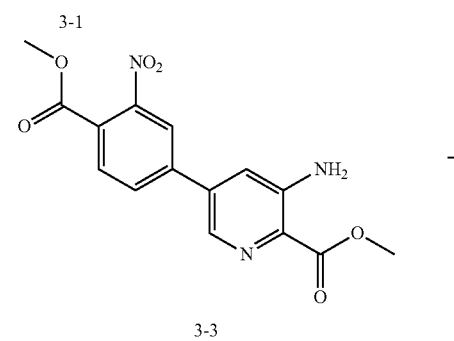

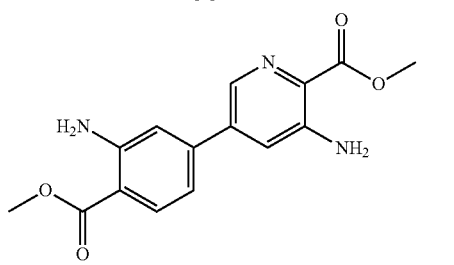

3

Step 1: Synthesis of Compound 3-3

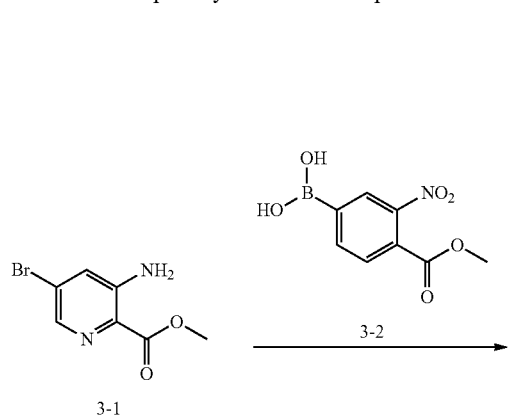

3-1

3-3

Compounds 3-1 (300 mg, 1.30 mmol, 1 eq) and 3-2 (379.73 mg, 1.69 mmol, 1.3 eq), potassium phosphate (551.24 mg, 2.60 mmol, 2 eq) and [1,1'-bis(diphenylphosphino) ferrocene] palladium (II) dichloromethane (530.18 mg, 649.22 µmol, 0.5 eq) were dissolved in dichloroethane (15 mL), and stirred at 80° C. for 15 hours. After the reaction was over, a reaction solution was filtered directly, and filtrate was spin-dried to obtain crude. The crude was purified by a rapid silica gel column (petroleum ether:ethyl acetate=100:0 to 50:50) to obtain Compound 3-3.

$^1$H NMR (400 MHz, CDCl$_3$) δ 8.29 (s, 1H), 8.08 (s, 1H), 7.88 (s, 2H), 7.25 (s, 1H), 5.95 (br s, 2H), 4.03 (s, 3H), 3.96 (s, 3H).

Step 2: Synthesis of Compound 3-4

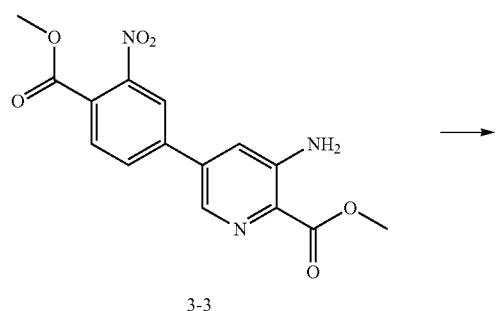

3-3

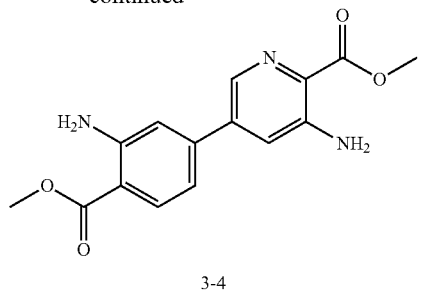

3-4

The Compound 3-3 (250 mg, 754.65 µmol, 1 eq) and hydrochloric acid (12 M, 1.26 mL, 20 eq) were dissolved in methanol (12 mL) and water (3 mL); reducing iron powders (421.43 mg, 7.55 mmol, 10 eq) were added, and stirred at 25° C. for 1 day and 15 hours. After the reaction was over, a reaction solution was adjusted to pH=9 with a saturated sodium carbonate aqueous solution (50 mL), and extracted with ethyl acetate (60 mL*2). After organic phases were combined, the organic phases were dried over anhydrous sodium sulfate and spin-dried to obtain crude. The crude was purified by a rapid silica gel column (petroleum ether:ethyl acetate=100:0 to 50:50) to obtain Compound 3-4.

$^1$H NMR (400 MHz, DMSO-d$_6$) δ 8.09 (d, J=2.01 Hz, 1H), 7.82 (d, J=8.28 Hz, 1H), 7.43 (d, J=2.01 Hz, 1H), 7.08 (d, J=1.51 Hz, 1H), 6.71-6.86 (m, 5H), 3.83 (d, J=5.77 Hz, 6H).

Step 3: Synthesis of Compound 3

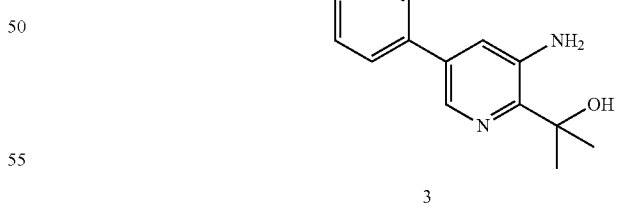

3-4

3

The Compound 3-4 (80 mg, 265.52 µmol, 1 eq) was dissolved in tetrahydrofuran (10 mL) and cooled to 0° C. Methyl magnesium bromide (33 M, 2 mL, 22.60 eq) was added dropwise in a 2-methyltetrahydrofuran solution at 0° C. The solution was reacted under stirring at 0° C. for 30 min, and then stirred at 25° C. for 15 hours. After the reaction was over, a reaction solution was quenched by adding a saturated amine chloride aqueous solution (20 mL), and then extracted in ethyl acetate (50 mL). The organic phases were dried over anhydrous sodium sulfate and spin-dried to obtain the crude. The crude was purified by thin-layer chromatographic silica gel plate separation (mobile phase: petroleum ether:ethyl acetate=2:5) to obtain Compound 3.

LCMS: [MS+H⁺]=301.9.

$^1$H NMR (400 MHz, CDCl$_3$) δ 8.12 (d, J=1.76 Hz, 1H), 7.20 (d, J=8.03 Hz, 1H), 7.07 (d, J=2.01 Hz, 1H), 6.85 (dd, J=2.01, 8.03 Hz, 1H), 6.81 (d, J=2.01 Hz, 1H), 4.31-5.07 (m, 4H), 3.32 (br s, 2H), 1.71 (d, J=5.27 Hz, 12H).

Example 4: Synthesis of Compound 4

The Compound 3-1 (3 g, 12.98 mmol, 1 eq) was dissolved in tetrahydrofuran (10 mL), a reaction temperature was reduced to −78° C., and lithium methyl (1 M, 64.92 mL, 5 eq) was added dropwise and stirred at −78° C. for 1 hour. TLC plate monitoring (petroleum ether:ethyl acetate=3:1) showed a new point generated in the reaction. A reaction solution was quenched by adding water (50 mL), and then extracted with ethyl acetate (50 mL*2). Organic phases were spin-dried. Products were purified by a rapid silica gel column (petroleum ether/ethyl acetate=3:1 to 1:1) to obtain Compound 4-2.

$^1$H NMR (400 MHz, CDCl$_3$) δ 7.93 (d, J=2.0 Hz, 1H), 7.06 (d, J=2.0 Hz, 1H), 4.67 (br s, 2H), 1.64 (s, 6H)

Step 2: Synthesis of Compound 4

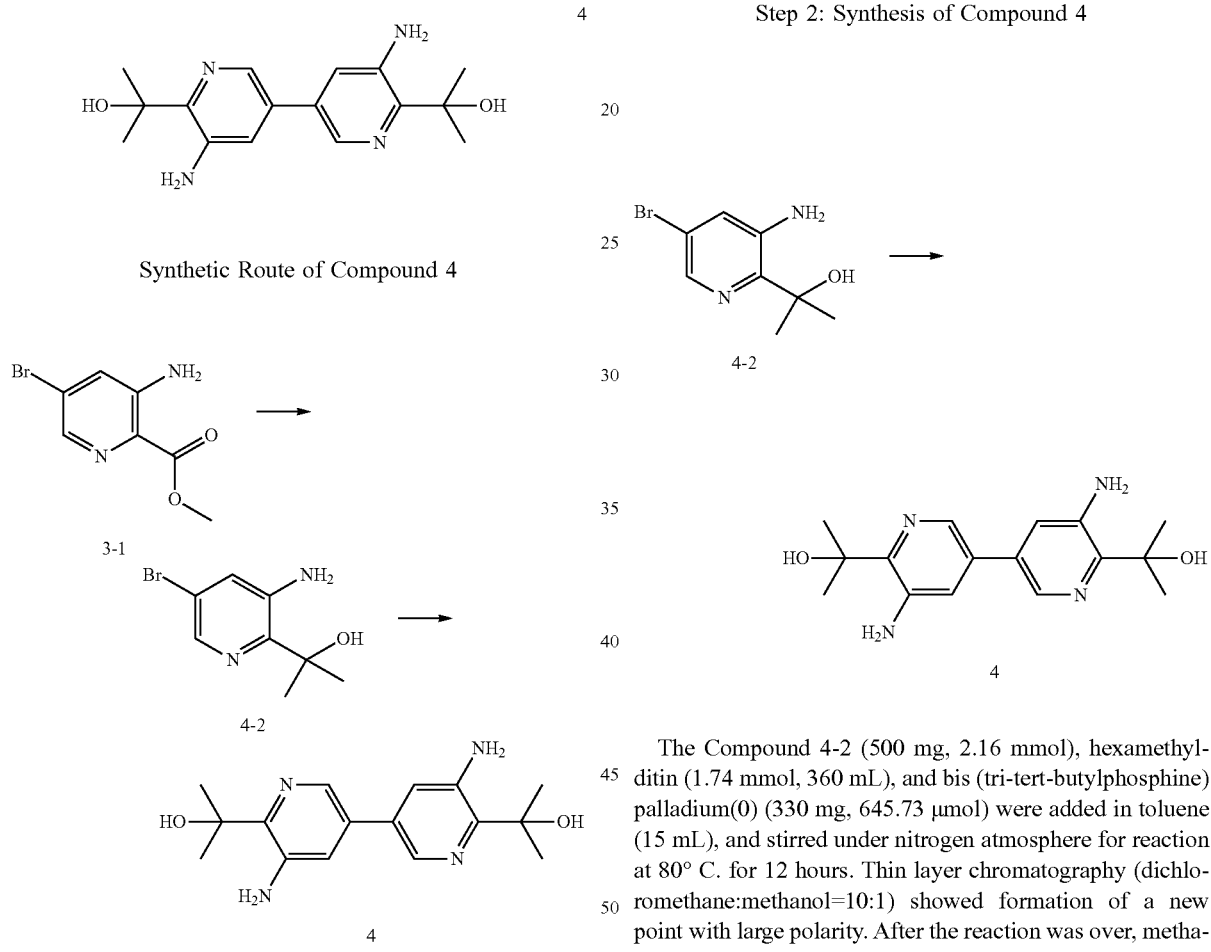

The Compound 4-2 (500 mg, 2.16 mmol), hexamethylditin (1.74 mmol, 360 mL), and bis (tri-tert-butylphosphine)palladium(0) (330 mg, 645.73 μmol) were added in toluene (15 mL), and stirred under nitrogen atmosphere for reaction at 80° C. for 12 hours. Thin layer chromatography (dichloromethane:methanol=10:1) showed formation of a new point with large polarity. After the reaction was over, methanol (10 mL) and the dichloromethane (100 mL) were added in the reaction; after solids were dissolved, the solids were filtered, and filtrate was concentrated under reduced pressure. The residue was subjected to column chromatography (dichloromethane:methanol=10:1) to obtain an impure product, and the impure product was separated by high performance liquid preparative chromatography (neutral, column: Waters Xbridge 150*25 mm 5 μm; mobile phase: [water (10 mM amine bicarbonate)-acetonitrile]; % B (acetonitrile): 10% -35%, 8.2 min) to obtain Compound 4.

LCMS (ESI): [M+H]⁺=303.

$^1$H NMR (400 MHz, DMSO-d$_6$) δ 7.91 (d, J=2.0 Hz, 2H), 7.12 (d, J=2.0 Hz, 2H), 5.68 (s, 4H), 5.48 (br s, 2H), 1.52 (m, 12H).

Example 5: Synthesis of Compound 5
Synthetic Route of Compound 5
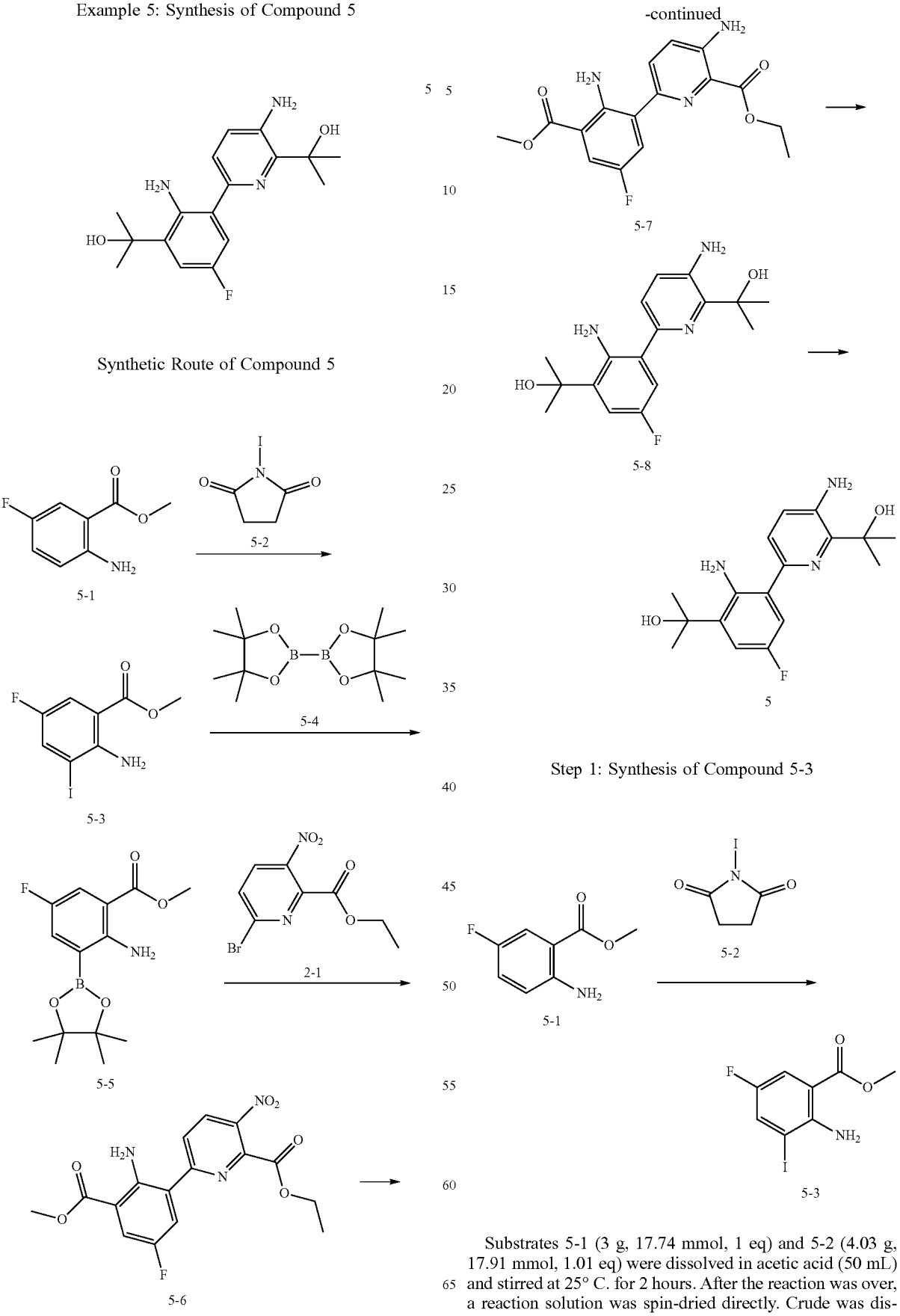
Step 1: Synthesis of Compound 5-3
Substrates 5-1 (3 g, 17.74 mmol, 1 eq) and 5-2 (4.03 g, 17.91 mmol, 1.01 eq) were dissolved in acetic acid (50 mL) and stirred at 25° C. for 2 hours. After the reaction was over, a reaction solution was spin-dried directly. Crude was dissolved in ethyl acetate (130 mL), and washed once with a saturated sodium carbonate aqueous solution (100 mL), sodium thiosulfate (100 mL, 1 M) and saturated saline (100 mL), respectively. The organic phases were dried over anhydrous sodium sulfate and spin-dried to obtain the crude. The crude was purified by a rapid silica gel column (petroleum ether:ethyl acetate=100:0 to 98:2) to obtain Compound 5-3.

¹H NMR (400 MHz, CDCl₃) δ 7.59-7.67 (m, 2H), 6.22 (br s, 2H), 3.90 (s, 3H).

Step 2: Synthesis of Compound 5-5

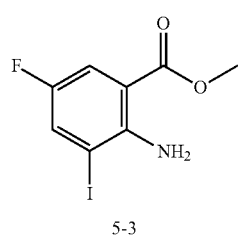

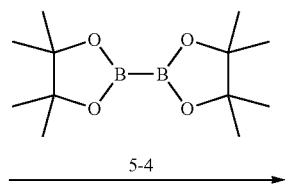

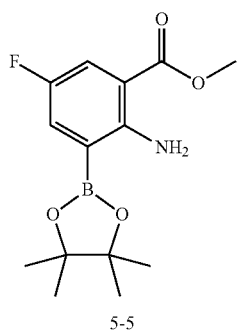

Compounds 5-3 (1 g, 3.39 mmol, 1 eq) and 5-4 (860.66 mg, 3.39 mmol, 1 eq) and potassium acetate (332.62 mg, 3.39 mmol, 1 eq) were dissolved in toluene (15 mL), and stirred under nitrogen atmosphere at 25° C. for 10 min; [1,1'-bis(diphenylphosphino) ferrocene] palladium (II) dichloromethane [Pd(dppf)Cl₂.CH₂Cl₂] (2.77 g, 3.39 mmol, 1 eq) was added. The solution was reacted under stirring for 15 hours after the temperature was increased to 100° C. After the reaction was over, a reaction solution was quenched by a saturated sodium carbonate aqueous solution (60 mL), and extracted with ethyl acetate (60 mL). Organic phases were washed with saturated saline (60 mL), dried over anhydrous sodium sulfate, and spin-dried to obtain crude. The crude was purified by a rapid silica gel column (petroleum ether:ethyl acetate=100:0 to 98.8:1.2) to obtain Compound 5-5.

LCMS: [MS+H⁺]=295.9.

Step 3: Synthesis of Compound 5-6

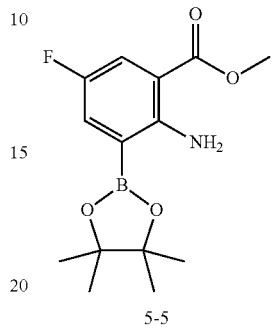

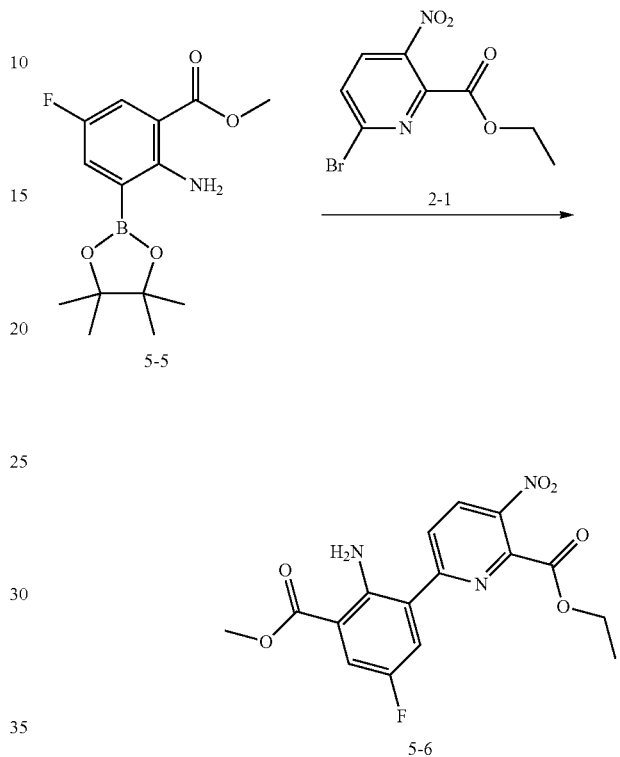

Compounds 2-1 (1.5 g, 5.45 mmol, 1 eq) and 5-5 (2.09 g, 7.09 mmol, 1.3 eq), potassium phosphate (3.47 g, 16.36 mmol, 3 eq) and Pd(dppf)Cl₂.CH₂Cl₂ (1.34 g, 1.64 mmol, 0.3 eq) were dissolved in dimethoxyethane (60 mL), and stirred at 80° C. for 15 hours. After the reaction was over, a reaction solution was filtered directly, and filtrate was spin-dried to obtain crude. The crude was purified by a rapid silica gel column (petroleum ether:ethyl acetate=100:0 to 60:40) to obtain Compound 5-6.

¹H NMR (400 MHz, CDCl₃) δ 8.46 (d, J=8.78 Hz, 1H), 8.12 (br s, 2H), 7.88 (d, J=8.78 Hz, 1H), 7.81 (dd, J=3.01, 9.03 Hz, 1H), 7.51 (dd, J=3.01, 9.03 Hz, 1H), 4.53 (q, J=7.03 Hz, 2H), 3.87-3.94 (m, 3H), 1.44 (t, J=7.15 Hz, 3H).

Step 4: Synthesis of Compound 5-7

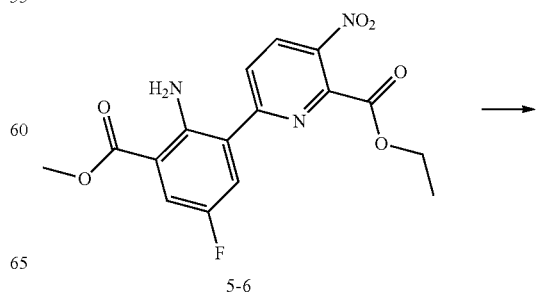

-continued

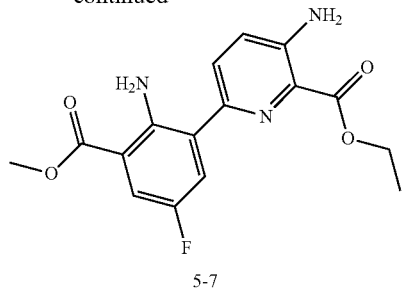

5-7

The Compound 5-6 (890 mg, 2.45 mmol, 1 eq) was dissolved in ethyl acetate (100 mL), under nitrogen atmosphere, Pd/C (500 mg, 10% purity) was added, and a hydrogen balloon (15 psi) was replaced by gas for three times. The solution was stirred at 25° C. for 15 hours, and then stirred at 65° C. for 15 hours. After the reaction was over, a reaction solution was filtered by diatomaceous earth. Filtrate was spin-dried directly to obtain Compound 5-7.

$^1$H NMR (400 MHz, CDCl$_3$) δ 8.54 (br s, 2H), 7.60-7.68 (m, 2H), 7.45 (dd, J=3.14, 9.66 Hz, 1H), 7.16 (d, J=8.78 Hz, 1H), 5.84 (br s, 2H), 4.42 (q, J=7.03 Hz, 2H), 3.90 (s, 3H), 1.45 (t, J=7.15 Hz, 3H).

Step 5: Synthesis of Compound 5-8

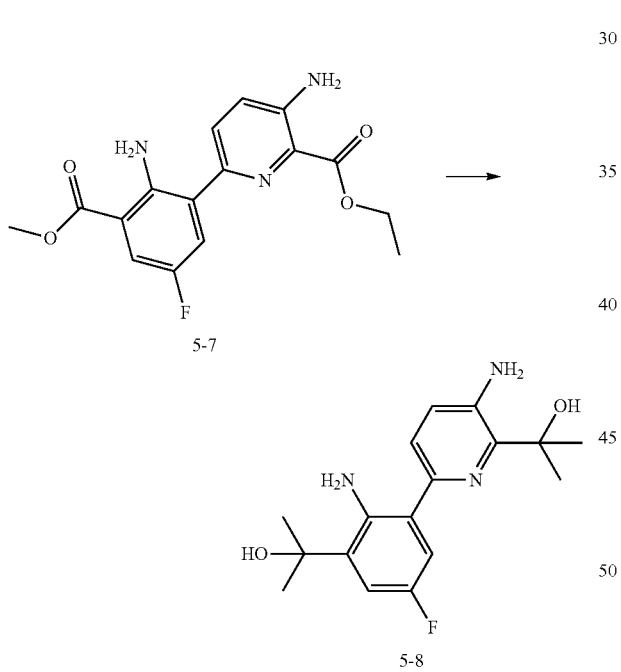

The Compound 5-7 (500 mg, 1.50 mmol, 1 eq) was dissolved in tetrahydrofuran (50 mL) and cooled to 0° C. Methyl magnesium bromide (3 M, 7.50 mL, 15 eq) was added dropwise in a 2-methyltetrahydrofuran solution at 0° C. The solution was reacted under stirring at 0° C. for 1.5 hours. After the reaction was over, a reaction solution was quenched by adding a saturated amine chloride aqueous solution (100 mL), and then extracted with ethyl acetate (100 mL*2). After organic phases were combined, the organic phases were dried over anhydrous sodium sulfate and spin-dried to obtain crude. The crude was purified by HPLC separation (column model: Boston Uni C18 40*150 mm*5 µm; mobile phase: [water (10 mM amine bicarbonate solution)-acetonitrile]; % B (acetonitrile): 28%-58%, 10 min) to obtain Compound 5-8.

$^1$H NMR (400 MHz, CDCl$_3$) δ 7.30 (d, J=8.28 Hz, 1H), 6.99-7.10 (m, 2H), 6.89 (dd, J=2.89, 10.16 Hz, 1H), 1.71 (d, J=1.76 Hz, 12H).

Step 6: Synthesis of Compound 5

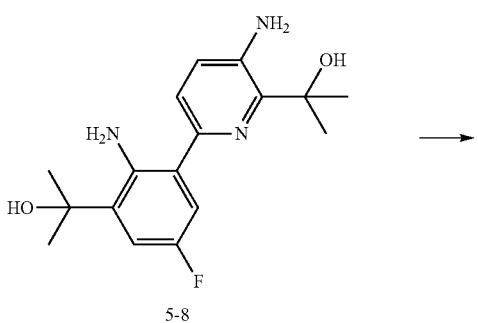

5-8

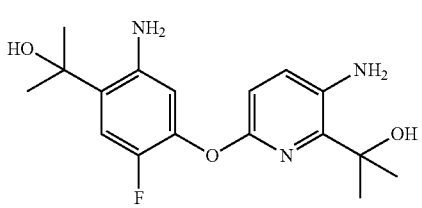

5

The Compound 5-8 (100 mg, 313.11 µmol, 1 eq) was dissolved in acetonitrile (5 mL), and then purified by separation with an HPLC machine (Column Model: Phenomenex Gemini-NX 150*30 mm*5 µm; mobile phase: [Water (0.04% amine aqueous solution+10 mM amine bicarbonate solution)-acetonitrile]; % B (acetonitrile): 39%-49%, 8 min) to obtain Compound 5.

$^1$H NMR (400 MHz, DMSO-d$_6$) δ 7.36 (d, J=8.53 Hz, 1H), 7.05-7.13 (m, 2H), 6.89 (s, 2H), 6.84 (dd, J=3.01, 10.54 Hz, 1H), 5.72 (s, 2H), 5.55 (s, 1H), 5.47 (s, 1H), 1.53 (d, J=4.02 Hz, 12H).

Example 6: Synthesis of Compound 6

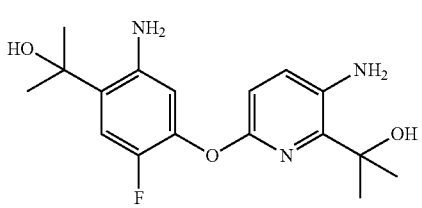

6

Synthetic Route of Compound 6

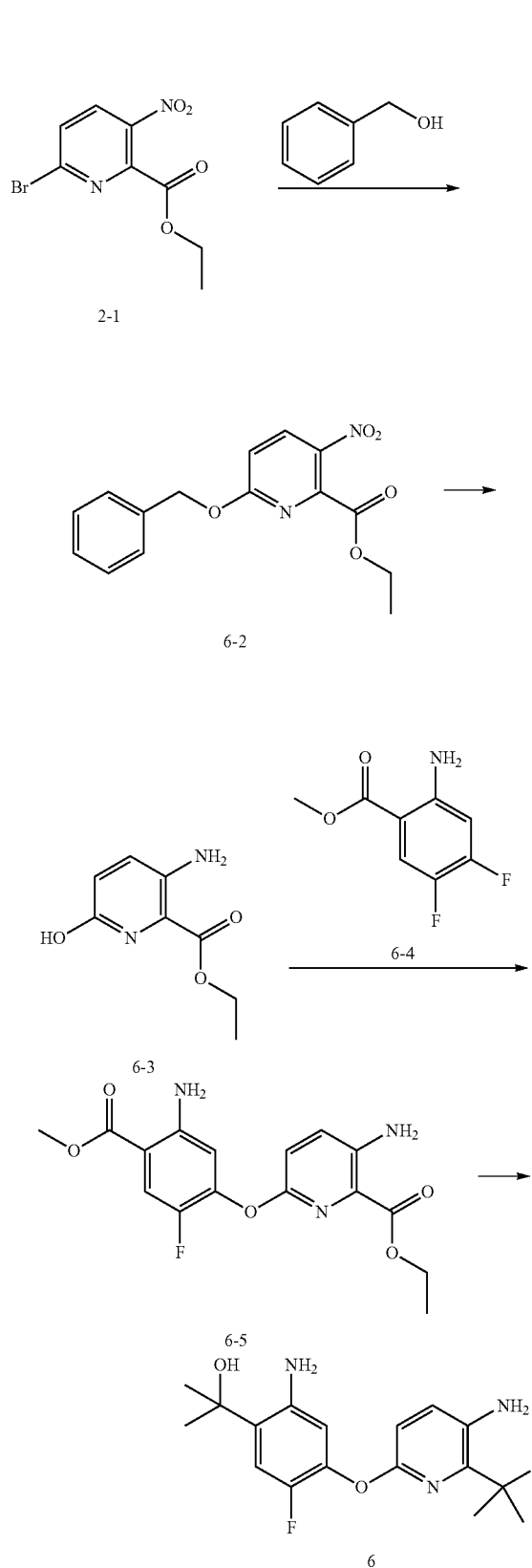

Step 1: Synthesis of Compound 6-2

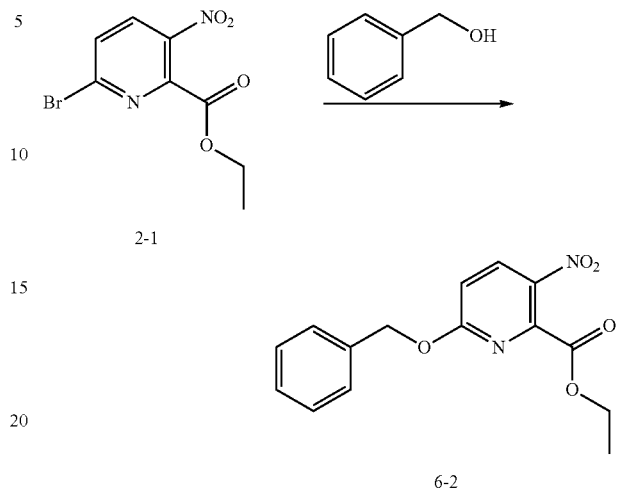

The Compound 2-1 (10 g, 36.36 mmol, 1 eq) and benzyl alcohol (7.86 g, 72.71 mmol, 7.56 mL, 2 eq) were dissolved in acetonitrile (100 mL), and cesium carbonate (23.69 g, 72.71 mmol, 2 eq) was added at 20° C.; the mixed solution was stirred at 20° C. for 12 hours. After the reaction was over, a reaction solution was quenched in water (40 mL), and extracted with ethyl acetate (80 mL*3). After organic phases were combined, the organic phases were dried over anhydrous sodium sulfate, filtered, and spin-dried to obtain crude. The crude was purified by a rapid silica gel column (SiO$_2$, petroleum ether/ethyl acetate=5:1 to 3:1) to obtain Compound 6-2.

$^1$H NMR (400 MHz, CDCl$_3$): δ 8.39-8.33 (m, 1H), 7.48-7.38 (m, 5H), 6.99-6.93 (m, 1H), 5.52-5.48 (m, 2H), 4.57-4.48 (m, 2H), 1.48-1.41 (m, 3H).

Step 2: Synthesis of Compound 6-3

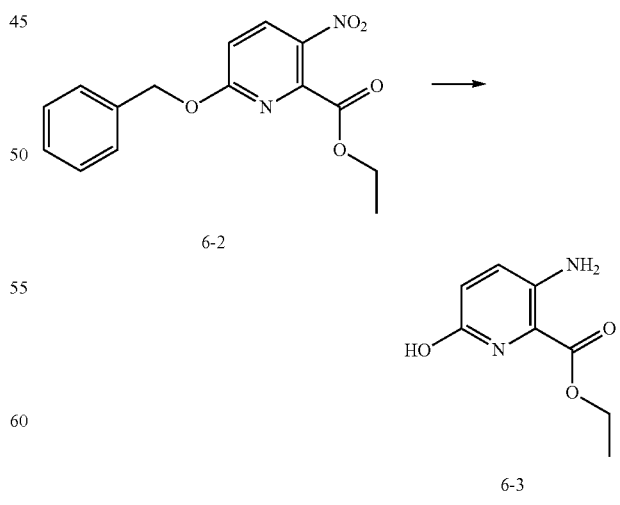

The Compound 6-2 (4.9 g, 16.21 mmol, 1 eq) was dissolved in ethanol (90 mL), under nitrogen atmosphere, palladium on carbon (Pd/C, 0.5 g, 16.21 mmol, 10% purity, 1 eq) was added, and a hydrogen balloon as replaced by gas for three times. The solution was stirred at 30° C. for 12 hours. After the reaction was over, a reaction solution was filtered, and filtrate was spin-dried to obtain crude. The crude was purified by a rapid silica gel column (SiO₂, dichloromethane:methanol=10:0 to 10:1) to obtain Compound 6-3.

¹H NMR (400 MHz, CDCl₃): δ 9.17 (br s, 1H), 7.10 (d, J=9.8 Hz, 1H), 6.73 (d, J=9.8 Hz, 1H), 5.41 (br s, 2H), 4.36 (q, J=7.0 Hz, 2H), 1.38 (t, J=7.2 Hz, 3H).

Step 3: Synthesis of Compound 6-5

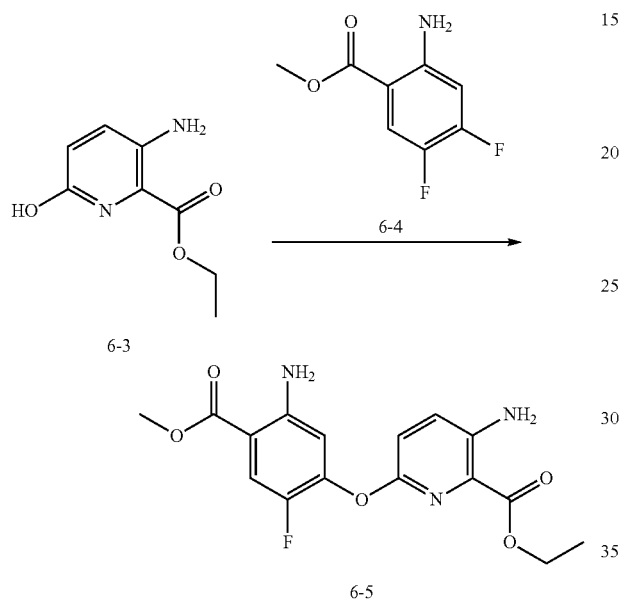

The Compounds 6-4 (1 g, 5.34 mmol, 1 eq) and 6-3 (974.4 mg, 5.35 mmol, 1 eq) were dissolved in DMSO (20 mL), potassium phosphate (1.70 g, 8.00 mmol, 1.5 eq) was added, and the solution was stirred at 100° C. for 12 hours. After the reaction was over, a reaction solution was diluted in ethyl acetate (50 mL), and washed with water (30 mL*2) and saturated saline (30 mL) sequentially. Organic phases were dried over anhydrous sodium sulfate, filtered, and spin-dried to obtain crude. The crude was purified by a rapid silica gel column (SiO₂, petroleum ether/ethyl acetate=5:1 to 2:1) to obtain Compound 6-5.

¹H NMR (400 MHz, CDCl₃) δ 7.64 (d, J=11.8 Hz, 1H), 7.21-7.13 (m, 1H), 7.02-6.97 (m, 1H), 6.56 (d, J=6.8 Hz, 1H), 4.44-4.31 (m, 2H), 3.89 (s, 3H), 1.40 (t, J=7.2 Hz, 3H).

Step 4: Synthesis of Compound 6

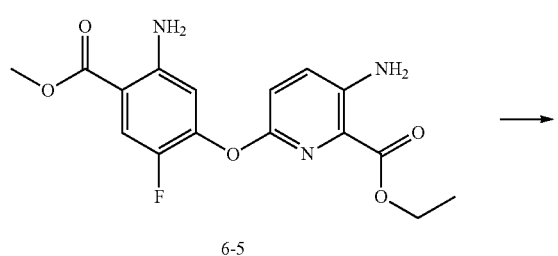

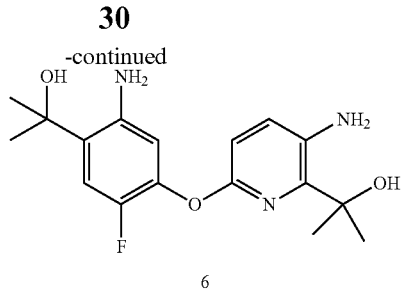

The Compound 6-5 (200 mg, 572.55 μmol, 1 eq) was dissolved in tetrahydrofuran (40 mL) and cooled to 0° C. Methyl magnesium bromide (3 M, 5 mL, 26.20 eq) was added dropwise in a 2-methyltetrahydrofuran solution at 0° C. The solution was reacted under stirring at 0° C. for 1 hour, and then stirred at 15° C. for 15 hours. After the reaction was over, a reaction solution was quenched by adding a saturated amine chloride aqueous solution (50 mL), and then extracted in ethyl acetate (60 mL). The organic phases were dried over anhydrous sodium sulfate and spin-dried to obtain the crude. The crude was purified by HPLC separation (column model: Waters Xbridge 150*25 mm 5 μm; mobile phase: [water (10 mM amine bicarbonate solution)-acetonitrile]; % B (acetonitrile): 15%-45%, 10 min) to obtain Compound 2.

LCMS: [MS+H⁺]=336.0.

¹H NMR (400 MHz, DMSO-d₆) δ 7.06 (d, J=8.28 Hz, 1H), 6.88 (d, J=13.05 Hz, 1H), 6.55 (d, J=8.28 Hz, 1H), 6.33 (d, J=7.53 Hz, 1H), 5.37 (s, 1H), 5.30 (br d, J=3.01 Hz, 4H), 5.26 (s, 1H), 1.48 (s, 6H), 1.38 (s, 6H).

Example 7: Synthesis of Compound 7

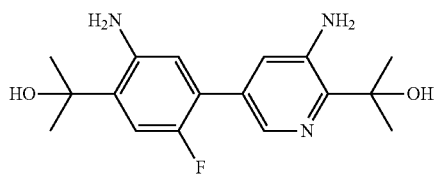

Synthetic Route of Compound 7

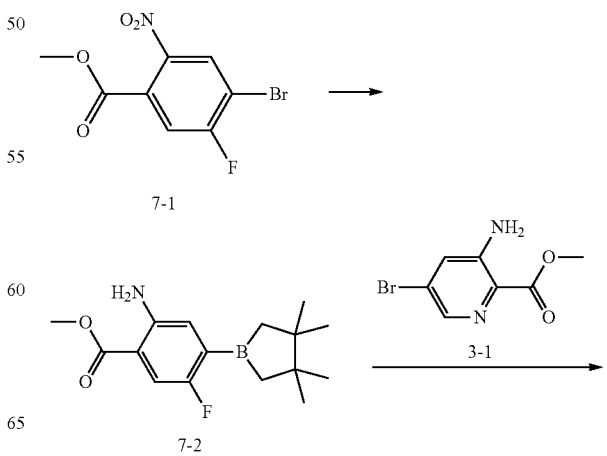

-continued

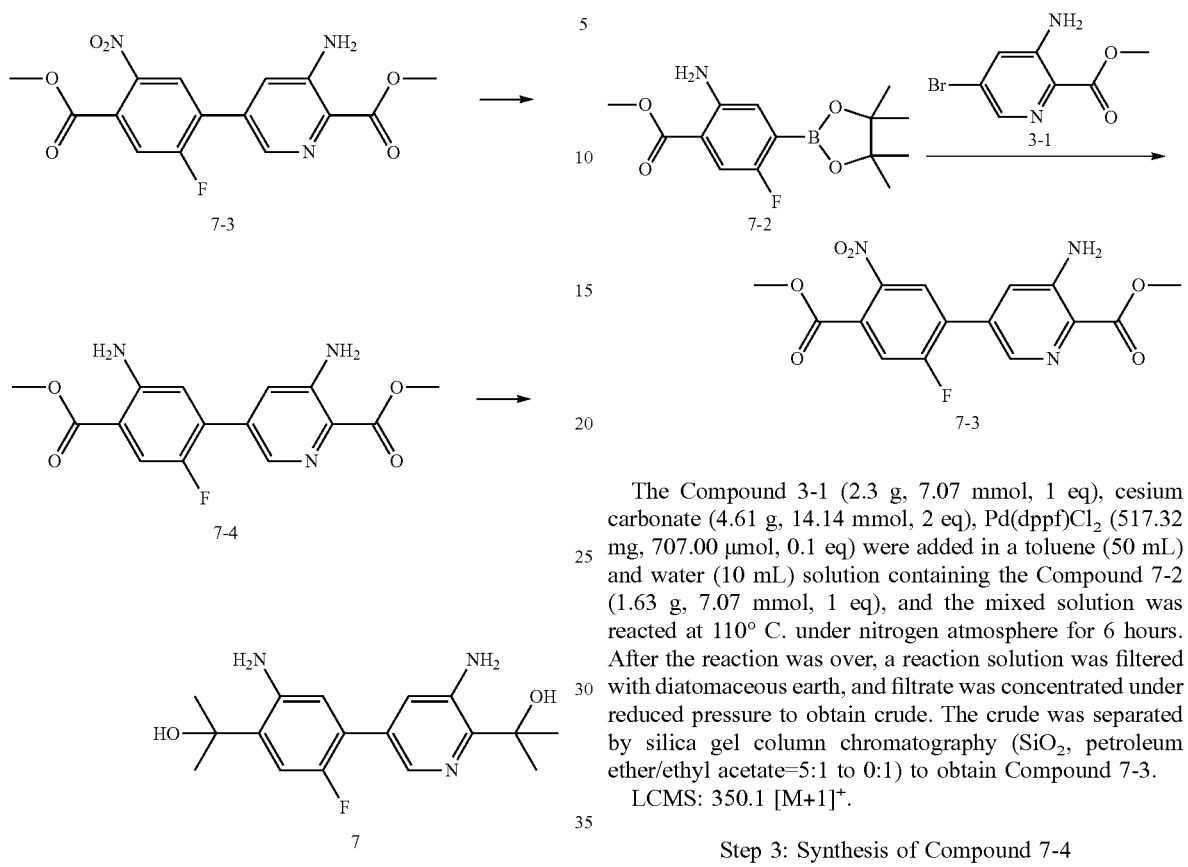

Step 2: Synthesis of Compound 7-3

The Compound 3-1 (2.3 g, 7.07 mmol, 1 eq), cesium carbonate (4.61 g, 14.14 mmol, 2 eq), Pd(dppf)Cl$_2$ (517.32 mg, 707.00 μmol, 0.1 eq) were added in a toluene (50 mL) and water (10 mL) solution containing the Compound 7-2 (1.63 g, 7.07 mmol, 1 eq), and the mixed solution was reacted at 110° C. under nitrogen atmosphere for 6 hours. After the reaction was over, a reaction solution was filtered with diatomaceous earth, and filtrate was concentrated under reduced pressure to obtain crude. The crude was separated by silica gel column chromatography (SiO$_2$, petroleum ether/ethyl acetate=5:1 to 0:1) to obtain Compound 7-3.
LCMS: 350.1 [M+1]$^+$.

Step 3: Synthesis of Compound 7-4

Step 1: Synthesis of Compound 7-2

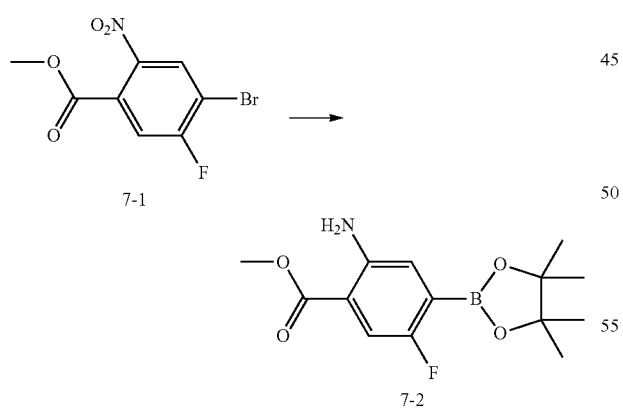

The Compound 5-4 (3.65 g, 14.39 mmol, 2 eq), Pd(dppf)Cl$_2$ (526.35 mg, 719.34 μmol, 0.1 eq), and potassium acetate (1.41 g, 14.39 mmol, 2 eq) were added in a toluene (30 mL) solution containing the Compound 7-1 (2 g, 7.19 mmol, 1 eq), and the mixed solution was reacted at 110° C. for 3 hours. After the reaction was over, a reaction solution was concentrated under reduced pressure to obtain crude 7-2.

Pd/C (1.7 g, 5% purity) was added in a methanol (50 mL) and ethyl acetate (50 mL) solution containing the Compound 7-3 (1.58 g, 4.52 mmol, 1 eq), and the mixed solution was reacted at 15 psi under hydrogen atmosphere at 20° C. for 3 hours. After the reaction was over, a reaction solution was filtered with diatomaceous earth, and filtrate was concentrated under reduced pressure to obtain Compound 7-4.
LCMS: 320 [M+1]$^+$.
$^1$H NMR (400 MHz, DMSO-d$_6$) δ ppm 7.96 (t, J=1.76 Hz, 1H), 7.54 (d, J=11.84 Hz, 1H), 7.39 (s, 1H), 6.95 (d, J=6.58 Hz, 1H), 6.82 (s, 2H), 6.66 (s, 2H), 3.83 (d, J=3.96 Hz, 6H).

Step 4: Synthesis of Compound 7

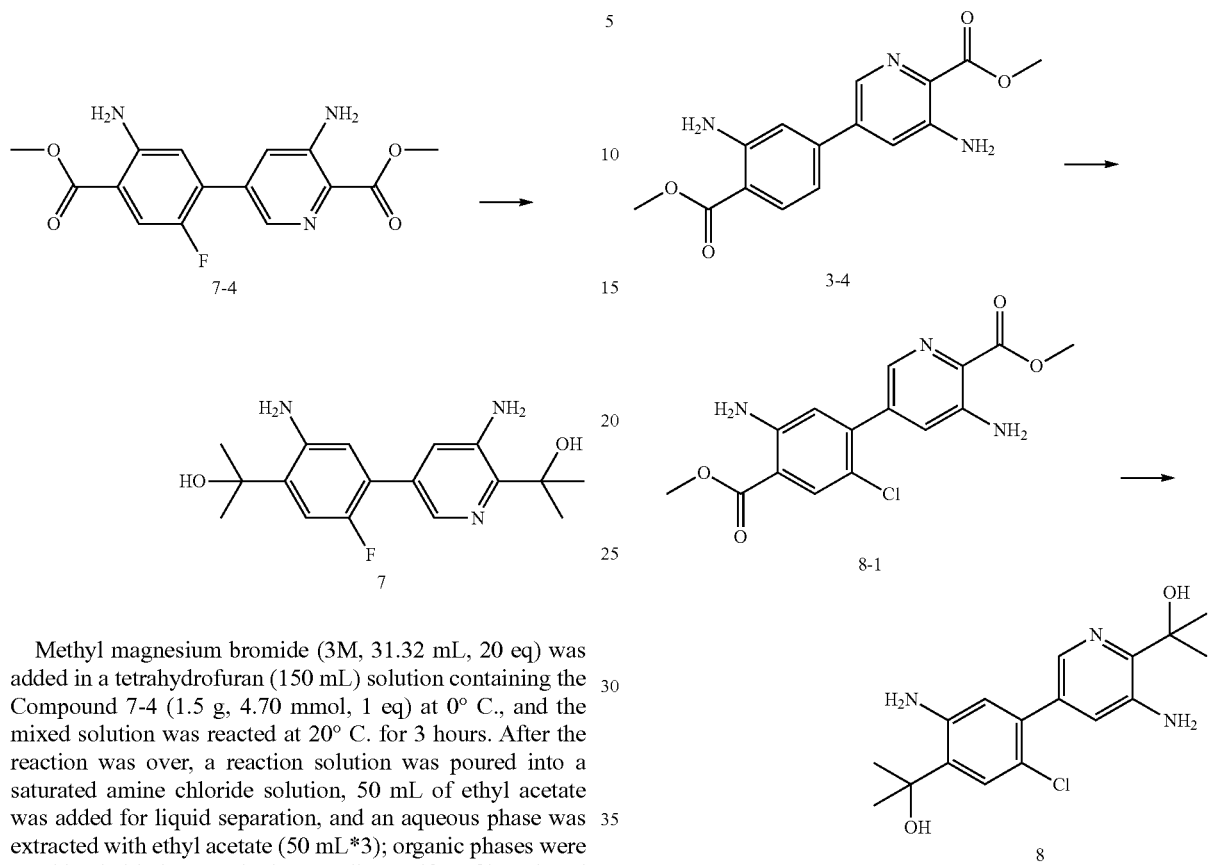

Methyl magnesium bromide (3M, 31.32 mL, 20 eq) was added in a tetrahydrofuran (150 mL) solution containing the Compound 7-4 (1.5 g, 4.70 mmol, 1 eq) at 0° C., and the mixed solution was reacted at 20° C. for 3 hours. After the reaction was over, a reaction solution was poured into a saturated amine chloride solution, 50 mL of ethyl acetate was added for liquid separation, and an aqueous phase was extracted with ethyl acetate (50 mL*3); organic phases were combined, dried over anhydrous sodium sulfate, filtered, and concentrated under reduced pressure to obtain crude. The crude was separated by HPLC (column model: Xtimate C18 150*25 mm*5 μm; mobile phase: [water (10 mM amine bicarbonate solution)-acetonitrile]; % B (acetonitrile): 25%-45%, 10.5 min) to obtain Compound 7.

LCMS: 320.0 [M+1]$^+$;

$^1$H NMR (400 MHz, DMSO-d$_6$) δ ppm 7.77 (s, 1H), 7.05 (s, 1H), 6.91 (d, J=12.28 Hz, 1H), 6.67 (d, J=7.46 Hz, 1H), 5.63 (s, 2H), 5.27-5.48 (m, 4H), 1.51 (s, 12H)

Example 8: Synthesis of Compound 8

Synthetic Route of Compound 8

Step 1: Synthesis of Compound 8-1

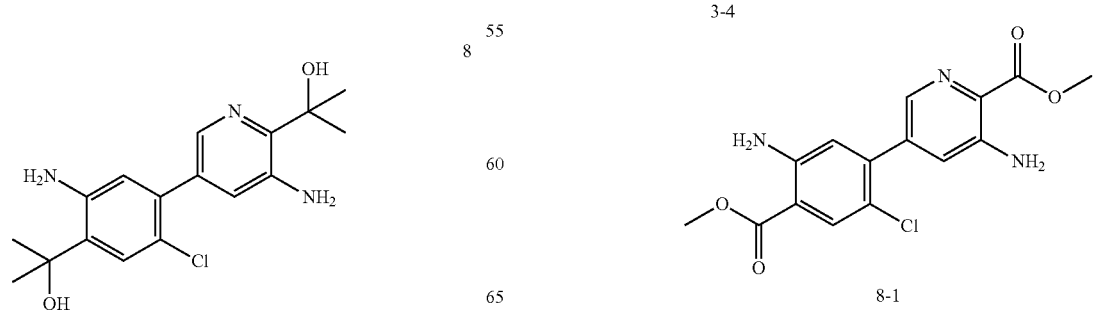

The Compound 3-4 (1 g, 3.32 mmol, 1 eq) and NCS (509.67 mg, 3.82 mmol, 1.15 eq) were dissolved in glacial acetic acid (60 mL), and stirred at 25° C. for 15 hours. After the reaction was over, a reaction solution was adjusted to pH about 9 with a saturated sodium carbonate aqueous solution (200 mL), and extracted with ethyl acetate (150 mL). The organic phase was washed once with saturated saline (50 mL), then dried over anhydrous sodium sulfate, and spin-dried to obtain crude. The crude was purified by a rapid silica gel column (petroleum ether:ethyl acetate=100:0 to 70:30) to obtain Compound 8-1.

$^1$H NMR (400 MHz, CDCl$_3$) δ 8.10 (d, J=1.76 Hz, 1H), 7.97 (s, 1H), 7.12 (d, J=1.76 Hz, 1H), 6.63 (s, 1H), 5.83 (br s, 4H), 4.01 (s, 3H), 3.91 (s, 3H).

Step 2: Synthesis of Compound 8

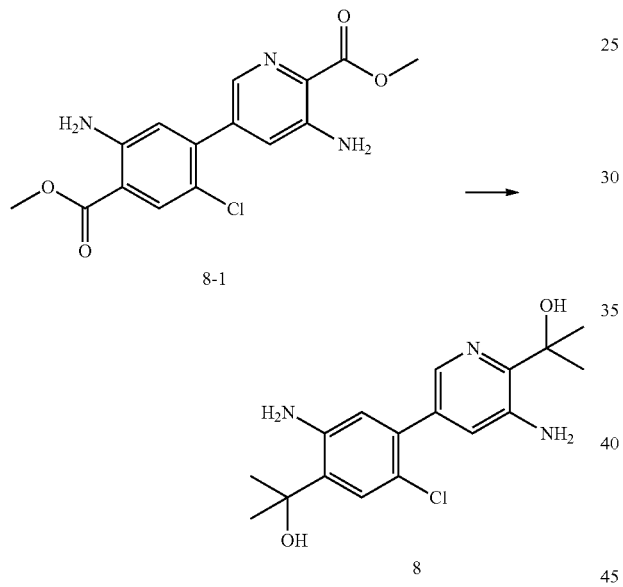

The Compound 8-1 (265 mg, 789.30 μmol, 1 eq) was dissolved in tetrahydrofuran (50 mL) and cooled to 0° C. Methyl magnesium bromide (3 M, 4 mL, 15.20 eq) was added dropwise in a 2-methyltetrahydrofuran solution at 0° C. The solution was reacted under stirring at 0° C. for 2 hours, and then stirred at 25° C. for 15 hours. After the reaction was over, a reaction solution was quenched by adding a saturated amine chloride aqueous solution (50 mL), and then extracted with ethyl acetate (60 mL*2). After organic phases were combined, the organic phases were dried over anhydrous sodium sulfate and spin-dried to obtain crude. The crude was purified by HPLC separation (column model: waters Xbridge 150*25 mm*5 μm; mobile phase: [water (10 mM amine bicarbonate solution)-acetonitrile]; % B (acetonitrile):25%-48%, 7.8 min) to obtain Compound 8.

LCMS: [MS+H+]=336.0;

$^1$H NMR (400 MHz, DMSO-d$_6$) δ 7.66 (d, J=2.01 Hz, 1H), 7.07 (s, 1H), 6.96 (d, J=2.01 Hz, 1H), 6.61 (s, 1H), 5.61 (br d, J=17.32Hz, 4H), 5.47 (s, 1H), 5.34 (s, 1H), 1.51 (s, 12H).

Example 9: Synthesis of Compound 9

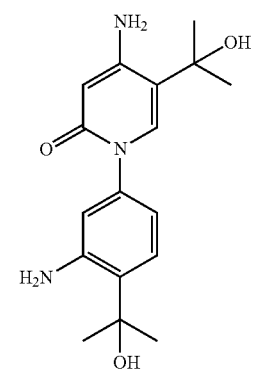

Synthetic Route of Compound 9

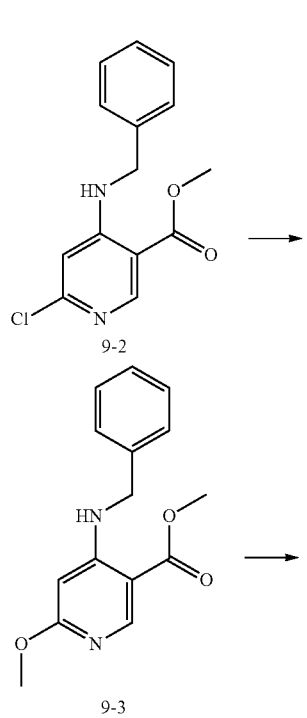

-continued

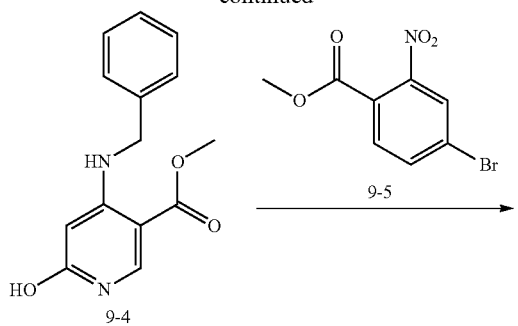 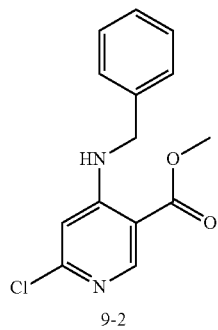

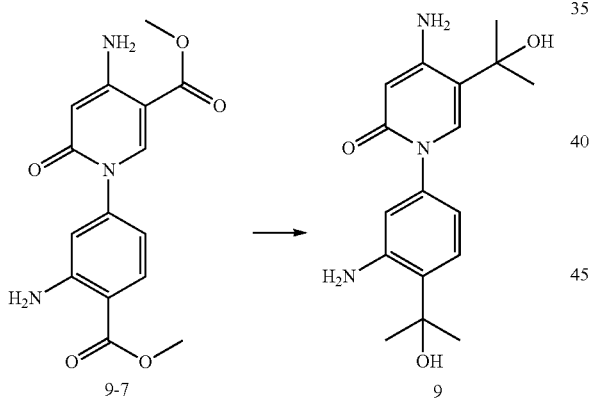

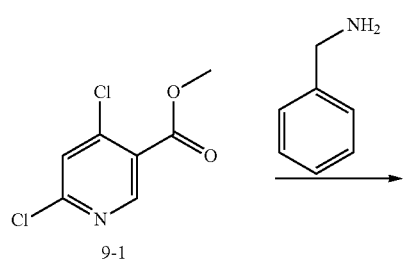

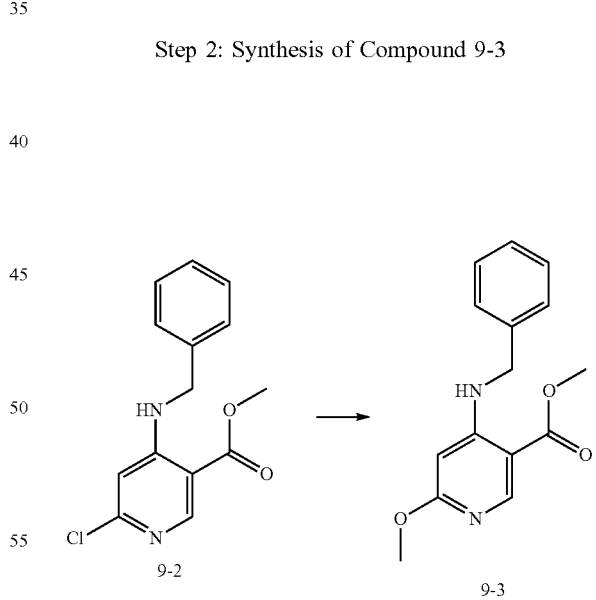

Step 1: Synthesis of Compound 9-2

A Compound 9-1 (24.8 g, 120.37 mmol, 1 eq) and benzylamine (15.48 g, 144.45 mmol, 15.75 mL, 1.2 eq) were dissolved in DMF (200 mL), and triethylamine (36.54 g, 361.12 mmol, 50.26 mL, 3 eq) was added at 20° C. A reaction solution was stirred at 20° C. for 21 hours. After the reaction was complete, a reaction solution was quenched by adding water (250 mL), and then extracted with ethyl acetate (500 mL*2). Organic phases were spin-dried. Products were purified by a rapid silica gel column (SiO$_2$, petroleum ether/ethyl acetate=5:1 to 3:1) to obtain Compound 9-2.

LCMS (ESI): [M+H]$^+$: 277.1.

$^1$H NMR (400 MHz, CDCl$_3$) δ 8.71 (s, 1H), 8.55 (br s, 1H), 7.36-7.43 (m, 2H), 7.29-7.35 (m, 3H), 6.56 (s, 1H), 4.44 (d, J=5.52 Hz, 2H), 3.88-3.92 (m, 3H).

Step 2: Synthesis of Compound 9-3

The Compound 9-2 (5 g, 18.07 mmol, 1 eq) and sodium methoxide (9.76 g, 180.69 mmol, 10 eq) were dissolved in MeOH (50 mL), and stirred at 90° C. under nitrogen atmosphere for 15 hours. After the reaction was over, products were purified by a rapid silica gel column (SiO$_2$, petroleum ether/ethyl acetate=5:1 to 3:1) to obtain Compound 9-3.

LCMS (ESI): [M+H]+: 273.

Step 3: Synthesis of Compound 9-4

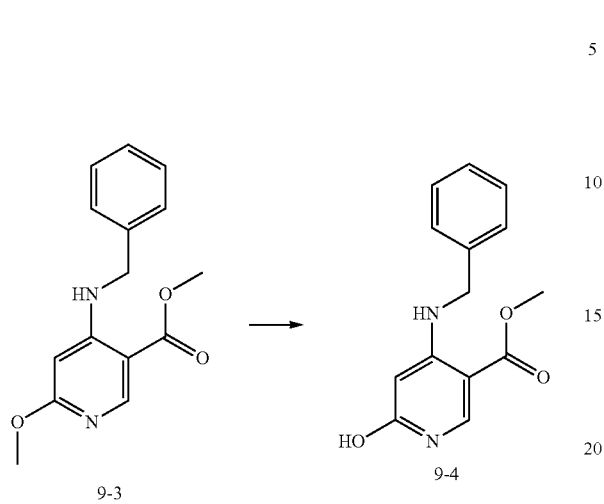

The Compound 9-3 (3.26 g, 11.97 mmol, 1 eq), trimethylchlorosilane (5.20 g, 47.89 mmol, 6.08 mL, 4 eq) and NaI (7.18 g, 47.89 mmol, 4 eq) were dissolved in acetonitrile (50 mL), and then reacted under stirring at 80° C. under nitrogen atmosphere for 15 hours. After the reaction was over, a reaction solution was adjusted to PH=7 with sodium bicarbonate, then quenched with water (20 mL), and extracted twice with dichloromethane (100 mL); finally organic phases were combined, and spin-dried in a rotary evaporator. Crude was purified with a rapid silica gel column (SiO$_2$, petroleum ether/ethyl acetate=5/1 to 3:1) to obtain Compound 9-4.

LCMS (ESI): [M+H]$^+$: 259.1

$^1$H NMR (400 MHz, CDCl$_3$) δ 7.47 (br s, 1H), 6.47-6.58 (m, 5H), 4.65 (s, 1H), 3.55 (br d, J=5.27 Hz, 2H), 3.00-3.08 (m, 3H)

Step 4: Synthesis of Compound 9-6

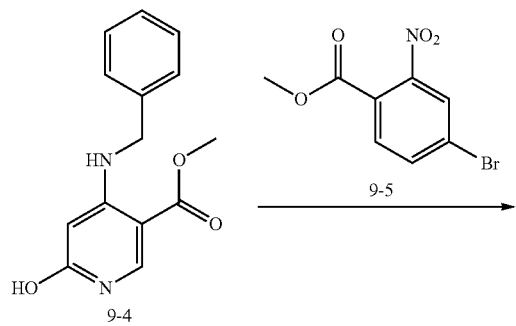

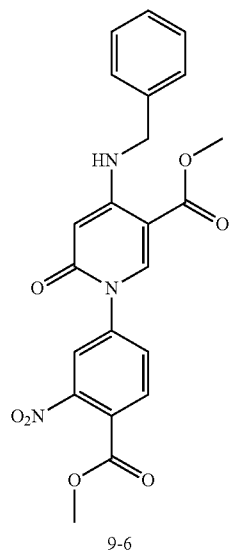

The Compound 9-4 (2.29 g, 8.87 mmol, 1 eq), the Compound 9-5 (2.77 g, 10.64 mmol, 1.2 eq), cuprous iodide (337.73 mg, 1.77 mmol, 0.2 eq), potassium carbonate (2.45 g, 17.73 mmol, 2 eq) and (1S, 2S)-N1, N2-dimethylcyclohexane-1,2-diamine (252.24 mg, 1.77 mmol, 0.2 eq) were dissolved in toluene (30 mL), and reacted under stirring at 110° C. under nitrogen atmosphere for 13 hours. After the reaction was over, the solution was filtered and spin-dried in the rotary evaporator. The crude was purified by a rapid silica gel column (SiO$_2$, petroleum ether/ethyl acetate=1:1 to 0:1) to obtain Compound 9-6.

LCMS (ESI): [M+H]$^+$: 438.1

Step 5: Synthesis of Compound 9-7

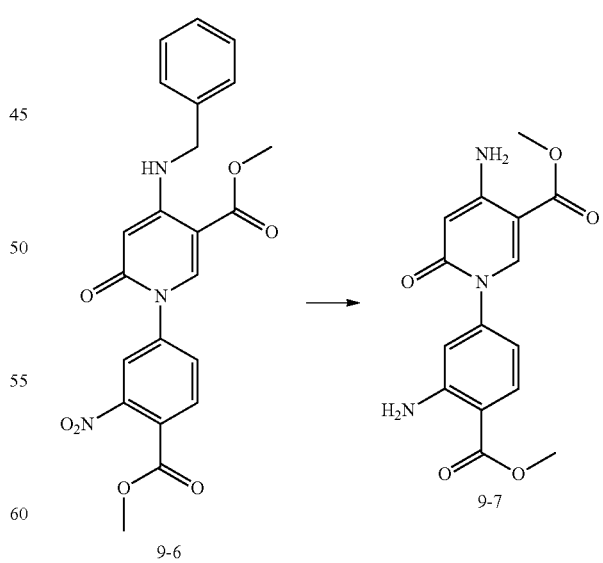

The Compound 9-6 (1 g, 2.29 mmol, 1 eq) was dissolved in tetrahydrofuran (30 mL), and palladium on carbon (1.5 g, 10% purity) was added in the mixed solution under nitrogen atmosphere. The mixed solution was stirred for 12 hours at 65° C. under hydrogen atmosphere. After the reaction was over, a reaction mixture was filtered and spin-dried. The crude was purified by a rapid silica gel column (SiO₂, petroleum ether/ethyl acetate=1:1 to 0:1) to obtain Compound 9-7.

LCMS (ESI): [M+H]⁺: 318.1

¹H NMR (400 MHz, DMSO-d₆) δ 8.12 (s, 1H), 7.76 (d, J=8.53 Hz, 1H), 7.06 (br s, 2H), 6.84 (s, 2H), 6.77 (d, J=1.76 Hz, 1H), 6.51 (dd, J=2.01, 8.53 Hz, 1H), 5.42 (s, 1H), 3.81 (s, 3H), 3.74 (s, 3H)

Step 6: Synthesis of Compound 9

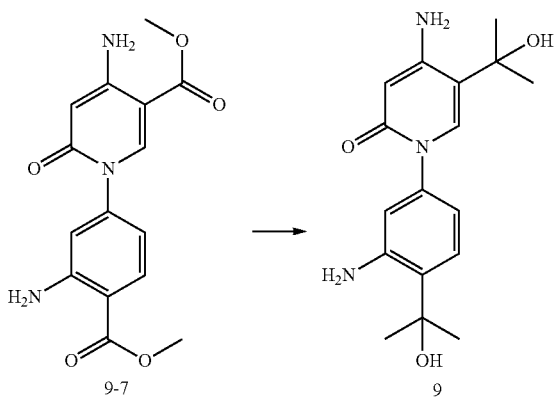 [SMILES: COC(=O)c1ccc(-n2cc(C(=O)OC)c(N)cc2=O)cc1N ; CC(C)(O)c1ccc(-n2cc(C(C)(C)O)c(N)cc2=O)cc1N]

The Compound 9-7 (200 mg, 630.33 μmol, 1 eq) was dissolved in tetrahydrofuran (20 mL); under nitrogen atmosphere, a reaction solution was cooled to −78° C. in a dry ice-ethanol bath, and lithium methyl (1.6 M, 5.91 mL, 15 eq) was slowly added dropwise. The reaction solution was slowly heated to 0° C. thereafter and stirred for 30 min. After the reaction was over, a reaction solution was quenched in water (10 mL) at 0° C., diluted with water (5 mL) and extracted with THF (40 mL). After organic phases were combined, the organic phases were dried over anhydrous sodium sulfate, filtered, and spin-dried to obtain Compound 9.

LCMS (ESI): [M+H]⁺: 318.

¹H NMR (400 MHz, DMSO-d₆) δ 6.20 (d, J=8.28 Hz, 1H), 6.14 (s, 1H), 5.69 (d, J=2.26 Hz, 1H), 5.53 (dd, J=2.13, 8.16 Hz, 1H), 5.45 (s, 2H), 4.73 (s, 2H), 4.57 (s, 1H), 4.53 (s, 1H), 4.41 (s, 1H), 0.67 (s, 6H), 0.60 (s, 6H).

Experimental Example 1: In Vitro Aldehyde Capture Capacity Test

1. Experiment Objective and Process

Objective: Xerophthalmia is caused by inflammation in eyes, wherein the inflammation may produce aldehydes that will accelerate the inflammation symptoms and worsen the xerophthalmia if not eliminated in time. In the experiment, a better compound was selected according to the complexing capacity of the drug and aldehydes in vivo by simulating the in vivo environment.

Procedures: Sulfobutyl-B-cyclodextrin (310 mg) was dissolved in a phosphate buffer (1.25 mL) to prepare a solution. Nonanal (5.0 mg, 32 μmol, 1.0 eq) and triolein (300 mg) were added to a reaction flask at room temperature, after addition of the prepared solution described above, linoleic acid (300 mg) was added, and finally a dimethyl sulfoxide (0.15 ml) solution containing the compound (32 μmol, 1.0 eq) of the present disclosure was added; the reaction solution was reacted at 20-23° C.

The reaction solution was reacted under stirring for 10 min, 100 min, 200 min, and 300 min respectively, and sampled for high performance liquid chromatography after the solution was stratified after standing for 2 min.

Sampling method: 25 μl of an upper emulsified layer and 50 μl of a lower aqueous phase were sampled by a pipette, and samples were diluted with 1 mL of methanol.

2. Test Results

The ultraviolet absorption of the nonanal was weak at 254 nm, so the nonanal had little overall effect on the content of complexed products. Therefore, the percentage contents of complexes at 254 nm under high performance liquid chromatography were compared to observe aldehyde capture and complexing capacities, as shown in FIG. 1 and Table 1:

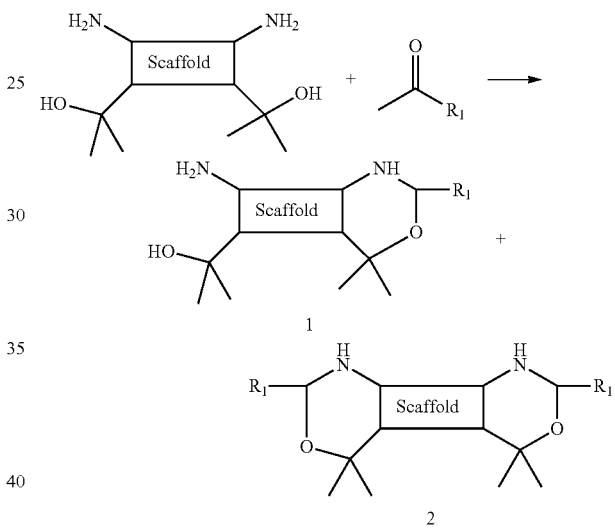

TABLE 1

Statistics of Test Results of Aldehyde Capture Capacity of the Compound

| Compound | Linear Equation | Slope | Regression Coefficient $R^2$ | Area under the curve AUC (min. Conversion) |
|---|---|---|---|---|
| Compound 1 | y = 0.0157x + 1.718 | 0.0157 | $R^2$ = 0.7521 | 1257 |
| Compound 2 | y = 0.0103x + 2.7459 | 0.0103 | $R^2$ = 0.9712 | 1271 |
| Compound 3 | y = 0.0652x + 3.362 | 0.0652 | $R^2$ = 0.9891 | 3979 |
| Compound 4 | y = 0.0589x + 1.3064 | 0.0589 | $R^2$ = 0.9964 | 3061 |
| Compound 5 | y = 0.0271x + 0.1945 | 0.0271 | $R^2$ = 0.9326 | 1208 |
| Compound 6 | y = 0.1083x + 12.77 | 0.1083 | $R^2$ = 0.9027 | 8953 |
| Compound 7 | y = 0.1002x + 7.7455 | 0.1002 | $R^2$ = 0.9686 | 6944 |
| Compound 8 | y = 0.0519x + 4.9828 | 0.0519 | $R^2$ = 0.9535 | 3879 |
| Compound 9 | y = 0.1241x + 14.964 | 0.1241 | $R^2$ = 0.9299 | 10284 |

The HPLC method is as follows: 2.5 μm, 3.0*100 mm 5-95 CD_XBEH_12 min_0.8.1 cm or XBRIGE 2.5 μm, 3.0*100 mm 5-80 CD_XBEH_12 min_0.8.1 cm Specific conditions: XBRIGE 2.5 μm, 3.0*100 mm 5-80 CD_XBEH_12 min_0.8.1 cm

| Column | XBridge BEHC18 3.0*100 mm, 2.5 μm |
|---|---|
| Detection Wavelength | 220, 254 nm |
| Column Temperature | 40° C. |
| Flow Rate | 0.8 mL/min |
| Injection Volume | 1 μL |
| Mobile Phase | A: 0.02% aqueous amine solution |
|  | B: Acetonitrile |

|  | Time (min) | A % | B % |
|---|---|---|---|
| Gradient elution | 0.01 | 95 | 5 |
|  | 6.00 | 40 | 60 |
|  | 9.00 | 20 | 80 |
|  | 12.00 | 20 | 80 |

XBRIGE 2.5 μm, 3.0*100 mm 5-95 CD_XBEH_12 min_0.8.1 cm

| Column | XBridge BEHC18 3.0*100 mm, 2.5 μm |
|---|---|
| Detection Wavelength | 220, 254nm |
| Column Temperature | 40° C. |
| Flow Rate | 0.8 mL/min |
| Injection Volume | 1 μL |
| Mobile Phase | A: 0.02% aqueous amine solution |
|  | B: Acetonitrile |

|  | Time (min) | A % | B % |
|---|---|---|---|
| Gradient elution | 0.01 | 95 | 5 |
|  | 6.00 | 15 | 85 |
|  | 9.00 | 5 | 95 |
|  | 12.00 | 5 | 95 |

Taking The compound 7 as an example, after 300 min of reaction, the analytical method for HPLC was XBRIGE 2.5 μm, 3.0*100mm 5-80 CD_XBEH_12 min_0.8.1 cm;

Retention time 6.689 min, 6.787 min, 6.966 min, and 7.102 min were absorption peaks of products complexed with monomolecular aldehyde;

Retention time 8.905 min, 9.010 min, and 9.075 min were absorption peaks of products complexed with bimolecular aldehyde.

The percentage content of the specific complexed product at 254 nm was calculated as the sum of the percentage contents of the absorption peaks for the retention time described above, i.e. (1.839+1.715+14.993+13.029)%+(1.004+2.212+1.247)%=36.039%

Specific HPLC data of the percentage contents of complexed products of the compounds of the present disclosure are shown in Table 2 below:

|  | Time (min) | | | |
|---|---|---|---|---|
| Compound | 10 | 100 | 200 | 300 |
| 1 | 0.917 | 4.909 | 4.383 | 6.224 |
| 4 | 1.475 | 7.663 | 13.353 | 18.636 |
| 2 | 2.658 | 4.097 | 4.721 | 5.796 |
| 3 | 3.265 | 10.569 | 17.191 | 22.182 |
| 5 | 0.882 | 2.935 | 4.328 | 9.139 |
| 7 | 6.634 | 20.013 | 29.424 | 36.039 |
| 6 | 9.738 | 27.850 | 37.847 | 41.686 |
| 8 | 4.117 | 12.121 | 15.49 | 19.873 |
| 9 | 12.268 | 31.427 | 43.086 | 48.761 |

Conclusion: Experiment results showed that the compounds of the present disclosure had far significant aldehydes complexing capability and speed.

Experimental Example 2: In Vitro Evaluation

Objective: To study the inhibitory effect of compounds on human liver microsomal cytochrome P450.

Experimental procedures: In the study on inhibition of the compounds on the human liver microsomal cytochrome P450 (CYP1A2, CYP2C9, CYP2C19, CYP2D6 and CYP3A4), fused human liver microsomes were selected as a CYP450 enzyme source. The compounds of different concentrations (10, 5, 1.5, 0.5, 0.15, 0.05, 0.015 mM) were incubated with probe substrates (where CYP3A4 employs two substrates) and cofactors (NADPH) of 5 CYP enzymes to determine the $IC_{50}$ value of each compound for inhibition of each CYP enzyme. Test results are as follows:

TABLE 3

Inhibition Test Results of Compounds of the Present Disclosure on Human Liver Microsomal Cytochrome P450 Isoenzymes

| Compound No. | CYP1A2/CYP2C9/CYP2C19/CYP2D6/CYP3A4(04) |
|---|---|
| Compound 3 | >50/>50/>50/>50/>50 |
| Compound 7 | >50/>50/>50/>50/>50 |
| Compound 8 | >50/>50/>50/>50/>50 |

Conclusion: The present disclosure has high safety and low possibility of drug interaction.

Experimental Example 3: Pharmacokinetic Evaluation of Compound

I

Objective: To study 5-Day toxicology of compounds in SD rats

Experimental materials: SD rats (male, 200-300 g, 7-9 weeks old, Shanghai Lingchang)

Experimental Procedures

Pharmacokinetic profiles of the compound were tested by intravenous injection in rodents according to the standard protocol. In the study, the candidate compound was prepared as a clear solution, and was administered to SD rats at 20 mg/kg by single intravenous injection for 5 consecutive days. A vehicle for intravenous injection was a 10% hydroxypropyl β-cyclodextrin aqueous solution. Whole blood samples were collected at 0.033, 0.083, 0.25, 0.5, 1, 2, 4, 8, and 24 hours postdose on Day 1 and Day 5 of dosing, centrifuged at 3000 r for 10 min, and separated from supernatant to obtain plasma samples. 15 μL of plasma samples were mixed with 300 μL of acetonitrile precipitated proteins containing an internal standard, and 2 μL of the supernatant was injected by centrifugation. Plasma concentrations were quantified by LC-MS/MS analysis, and pharmacokinetic parameters, such as clearance, half-life, and area under the concentration-time curve, were calculated.

Experiment Results

TABLE 4
Pharmacokinetic Test Results

| Test Sample | Clearance (mL/min/kg) | | Half-time $T_{1/2}$ (h) | | Area under the concentration-time curve AUC(nM · hr) | |
| --- | --- | --- | --- | --- | --- | --- |
| | Day 1 | Day 5 | Day 1 | Day 5 | Day 1 | Day 5 |
| Compound 3 | 7.11 | 9.04 | 2.45 | 2.72 | 155784 | 123277 |

Conclusion: The compound of the present disclosure has no risk of drug accumulation after injection for 5 consecutive days.

II

Objective: To study pharmacokinetics of the compound in Beagle dogs

Experimental material: Beagle dogs (male, 8-11 kg, greater than or equal to 6 months, Marshall)

Experimental Procedures

Pharmacokinetic profiles of the compound were tested by intravenous administration in rodents according to the standard protocol. In the study, the candidate compound was prepared as a clear solution, and was administered to Beagle dogs at 1 mg/kg by single intravenous injection. A vehicle for intravenous injection was a 10% hydroxypropyl β-cyclodextrin aqueous solution. Whole blood samples were collected at 0.033, 0.083, 0.25, 0.5, 1, 2, 4, 8, 12, and 24 hours, respectively, centrifuged at 3000 r for 10 min, and separated from supernatant to obtain plasma samples. 20 μL of plasma samples were mixed with 400 μL of acetonitrile precipitated proteins containing an internal standard, and 2 μL of the supernatant was injected by centrifugation. Plasma concentrations were quantified by LC-MS/MS analysis, and pharmacokinetic parameters, such as clearance, half-life, and area under the concentration-time curve, etc. were calculated.

Experiment Results

TABLE 5
Pharmacokinetic Test Results

| Test Sample | Clearance (mL/min/kg) | Half-time $T_{1/2}$ (h) | Area under the concentration-time curve AUC(nM · hr) |
| --- | --- | --- | --- |
| Compound 3 | 15 | 2.17 | 3709 |
| Compound 7 | 11.3 | 2.94 | 4672 |

Conclusion: The present disclosure has high clearance, moderate half-life and good pharmacokinetic profile.

III

Objective: To study pharmacokinetics of the compound in cynomolgus monkeys

Experimental material: Cynomolgus monkeys (male, 2.5-4 kg, greater than or equal to 2 years, Jingang Biotech)

Experimental Procedures

Pharmacokinetic profiles of the compound were tested by intravenous administration in monkeys according to the standard protocol. In the study, the candidate compound was prepared as a clear solution, and was administered to cynomolgus monkeys at 1 mg/kg by single intravenous injection. A vehicle for intravenous injection was a 10% hydroxypropyl β-cyclodextrin aqueous solution. Whole blood samples were collected at 0.033, 0.083, 0.25, 0.5, 1, 2, 4, 8, 12, and 24 hours, respectively, centrifuged at 3000 r for 10 min, and separated from supernatant to obtain plasma samples. 20 μL of plasma samples were mixed with 400 μL of acetonitrile precipitated proteins containing an internal standard, and 2 μL of the supernatant was injected by centrifugation. Plasma concentrations were quantified by LC-MS/MS analysis, and pharmacokinetic parameters, such as clearance, half-life, and area under the concentration-time curve, etc. were calculated.

Experiment Results

TABLE 6
Pharmacokinetic Test Results

| Test Sample | Clearance (mL/min/kg) | Half-time $T_{1/2}$ (h) | Area under the concentration-time curve AUC(nM · hr) |
| --- | --- | --- | --- |
| Compound 3 | 6.2 | 3.81 | 9164 |
| Compound 7 | 4.6 | 3.91 | 13016 |

Conclusion: The present disclosure has high clearance, moderate half-life and good pharmacokinetic profile.

Experimental Example 4: In Vivo Pharmacokinetic Study

Objective: To study the ratio of corneal to plasma drug concentration after eye drops in rats Experimental materials: Male SD rats, 200-300 g, 7-9 weeks old, Shanghai Lingchang Experimental procedures: The candidate compound was prepared as a clear solution, and administered to SD rats by eye drops. The vehicle for eye drops was 10% hydroxypropyl β-cyclodextrin aqueous solution, and the drug concentration in the eye drops was 5 mg/mL. Corneal and whole blood samples were collected at 1 and 4 hours, respectively. The corneal samples was homogenized in 15 mM phosphate buffer (PBS): MeoH (2:1, v:v) buffer, the whole blood samples were centrifuged at 3000 r for 10 min, and the supernatant plasma samples were separated. 20 μL of the plasma samples and homogenate samples were mixed with 400 μL of acetonitrile precipitated proteins containing an internal standard, respectively, and 2 μL of the supernatant was injected by centrifugation. The plasma concentrations were quantified by LC-MS/MS analysis; the drug concentrations in the cornea and plasma were measured respectively according to different time points, and the ratio of corneal/plasma concentrations was calculated.

Experiment Results

TABLE 7

Pharmacokinetic Test Results

| Test Sample | Time | Corneal Concentration (nM) | Plasma Concentration (nM) | Corneal Concentration/ Plasma Concentration C/P ratio |
|---|---|---|---|---|
| Compound 3 | 1 h | 1796 | 162 | 14.3 |
|  | 4 h | 581 | 43.8 | 16.6 |
| Compound 7 | 1 h | 2447 | 172 | 11.8 |
|  | 4 h | 330 | 24.4 | 12.4 |
| Compound 8 | 1 h | 1663 | 148 | 12.0 |
|  | 4 h | 167 | 36.4 | 3.72 |

Conclusion: As shown in the DMPK test, test compounds 3, 7 and 8 could enter the cornea by eye drops to show the efficacy. The ratio of cornea/plasma concentrations of the Compound 3 was relatively high (above 10). The drug took effect in the cornea, so the targeting property was good.

Experimental Example 5: In Vivo Efficacy Evaluation

Objective

Subcutaneous injection of scopolamine may induce the xerophthalmia in mice. Decreased tear secretion and inflammatory infiltration can be observed by tear tests and corneal fluorescence staining scores. It can predict whether a model can achieve the expected severity at the early stage of modeling.

Study Design

Twenty animals were selected from 25 female C57BL/6J mice and randomized into 4 groups by body weight via Provantis or Excel, 4 animals per group, and group assignment may also refer to the results of the tear test and the corneal fluorescence staining score of each animal prior to the experiment.

The mice were injected subcutaneously with scopolamine hydrobromide (3±0.5 h) for 4 times daily on Day 1 to Day 12 of the study to establish xerophthalmia models in the mice at 0.1 mL/animal/time.

On Day 1 to Day 13 of the study, animals were dosed by bilateral eye drops for 4 times daily (3±0.5 h) at 3 μL/eye (on Day 13, animals in Group 1 were not dosed). Each subcutaneous injection of the scopolamine hydrobromide was be given predose the eye drops (except examinations on Day 7 and Day 12).

Tear tests and corneal fluorescence staining scores were performed on all experimental animals on Day 7 and Day 12 prior to modeling.

Criteria for corneal fluorescence staining scores: The cornea of an animal was divided into 5 regions, i.e., superior, inferior, nasal, temporal and central regions, each with 0-3 scores. Each region was scored, and the monocular score was the sum of scores of the 5 regions. 0: no staining; 1: slight staining, punctate staining with less than 5 spots; 2: moderate staining, punctate staining but no plaque staining; 3: severe staining, marked fluorescent plaques.

The tear test was performed 30 min after the second dosing on Day 7 and Day 12 for all experimental animals, and the corneal fluorescence staining was scored for all experimental animals 30 min after the third dosing on Day 7 and Day 12.

TABLE 8

Efficacy Experiment Protocol of Scopolamine by Subcutaneous Injection in Mice

| Group | Number of animals (Female) | Modeling | Therapy Both eyes | Method of Administration |
|---|---|---|---|---|
| Vehicles | 4 | Subcutaneous | Vehicles | Eye drops |
| Compound 3 | 4 | injection of | 0.5% | 3 μl/eye |
| Compound 7 | 4 | scopolamine for 4 | 0.5% | 4 injections/day |
| Compound 8 | 4 | injections/day for 12 days (5 mg/mL, 0.1 mL/injection, 3 ± 0.5 h) | 0.3% | (3 ± 0.5 h) |

Figure 2:
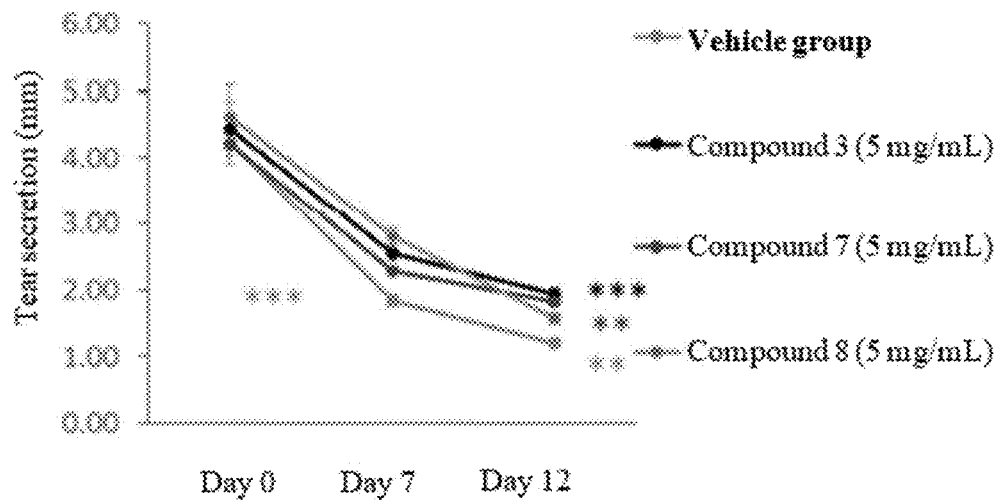
FIG. 2: Tear secretion results of an efficacy test on xerophthalmia in mice.
Figure 3:
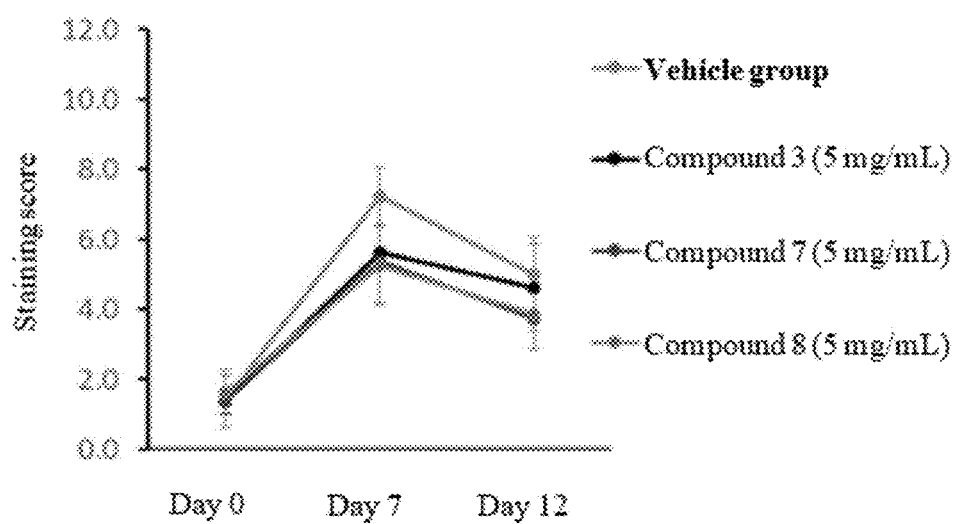
FIG. 3: Fluorescence staining results of cornea in an efficacy test on xerophthalmia in mice.

Test results: See FIG. 2 and FIG. 3 (Note:* in the attached drawings indicates P≤0.5,  indicates P≤0.01, and * indicates P≤0.001).

Conclusion: Under the conditions of the experiment, it can be seen that all tested compounds can improve tear secretion and corneal inflammation, showing the efficacy of improving the xerophthalmia.

What is claimed is:

1. A compound represented by formula (II) or a pharmaceutically acceptable salt thereof,

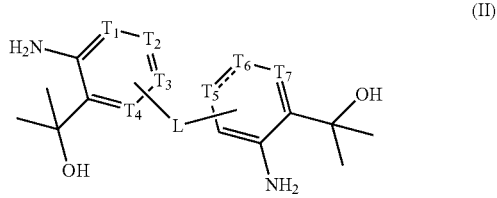

(II)

wherein

⚏ is selected from a single bond and a double bond;

$T_1$, $T_2$ and $T_3$ are each independently selected from C and $CR_1$;

$T_4$ is selected from N and $CR_1$;

$T_5$ is selected from C, $CR_5$, and C=O;

$T_6$ is selected from C and $CR_6$, $T_7$ is N; or, $T_6$ is N, $T_7$ is $CR_7$;

when $T_5$ is selected from C=O and $T_6$ is selected from N, then ⚏ is selected from a single bond;

L is selected from a single bond, —O—, and —CH$_2$—;

each $R_1$ is independently selected from H, F, Cl, Br, I, OH, and NH$_2$;

$R_5$, $R_6$ and $R_7$ are each independently selected from H, F, Cl, Br and I.

2. The compound or the pharmaceutically acceptable salt thereof as defined in claim 1, wherein the compound is selected from

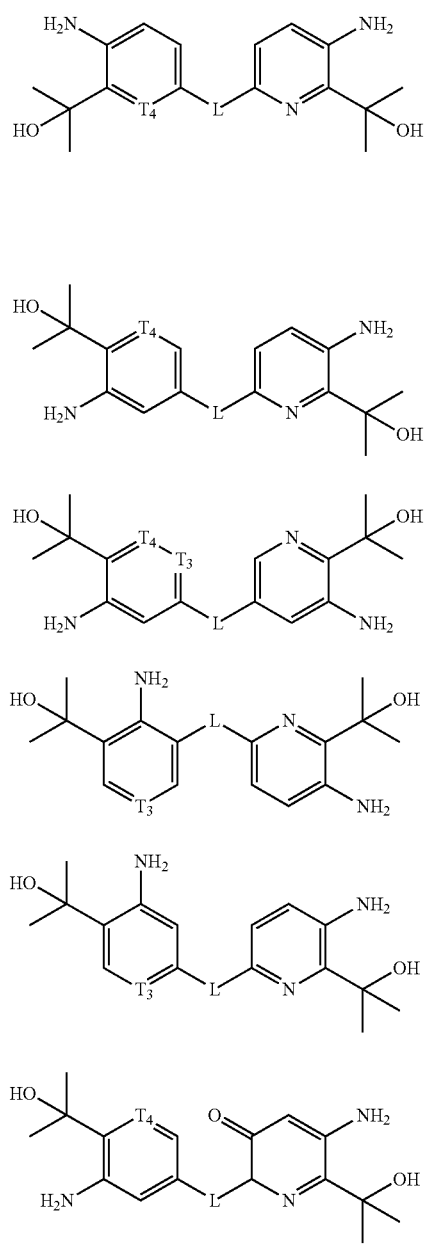
wherein
T$_3$ is CR$_1$;
T$_4$ is selected from N and CR$_1$.
3. The compound or the pharmaceutically acceptable salt thereof as defined in claim 2, wherein the compound is selected from
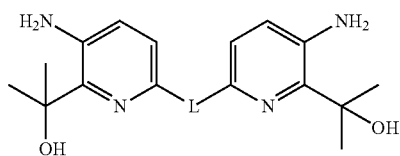
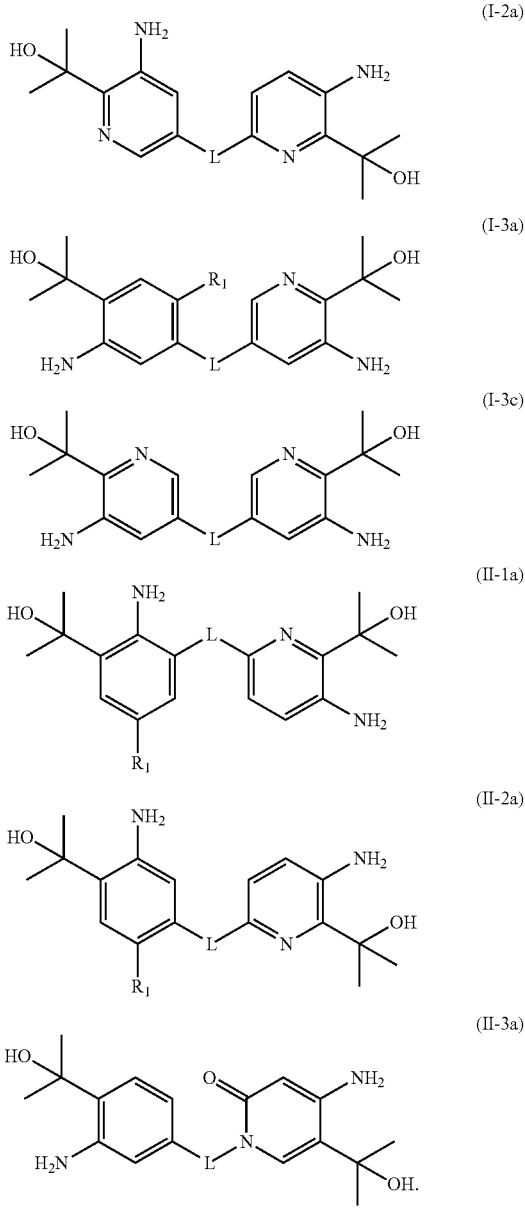
4. A compound represented by the following formula or a pharmaceutically acceptable salt thereof, wherein the compound is selected from:
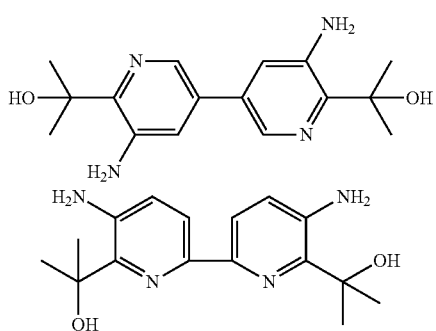

-continued

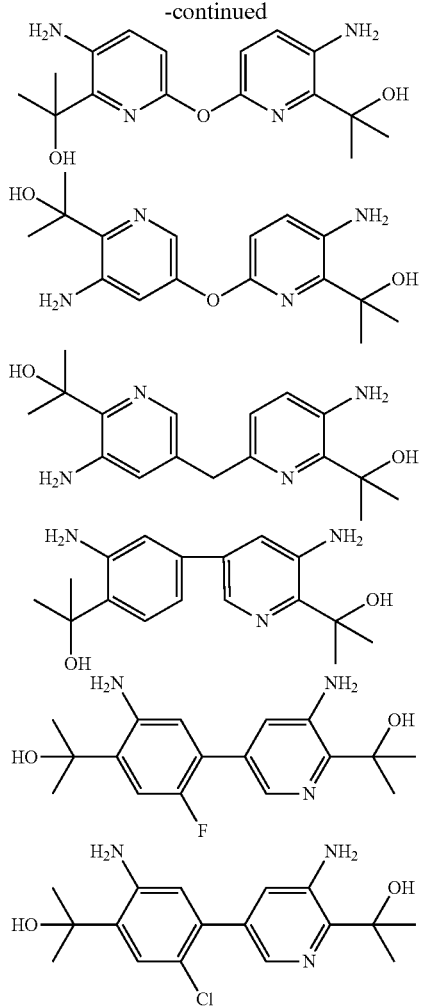

-continued

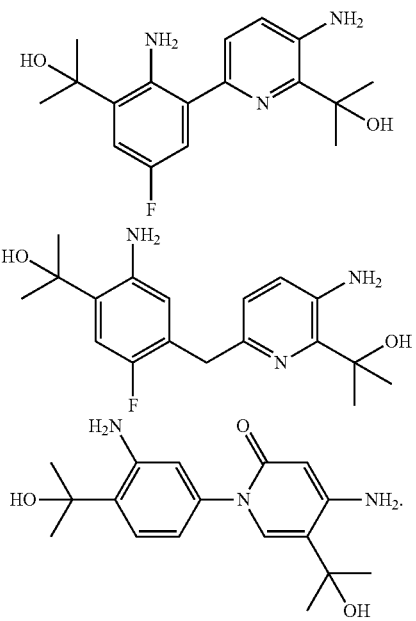

5. A pharmaceutical composition, comprising a therapeutically effective amount of the compound or the pharmaceutically acceptable salt thereof as defined in claim 1 as an active ingredient, and a pharmaceutically acceptable carrier thereof.

6. A method for binding the aldehydes in vivo in a subject in need thereof, comprising administering a therapeutically effective amount of the compound or the pharmaceutically acceptable salt thereof as defined in claim 1 to the subject.

* * * * *